United States Patent
Raslambekov

(10) Patent No.: US 11,328,809 B1
(45) Date of Patent: May 10, 2022

(54) SYSTEMS AND METHODS FOR MANUFACTURING AN ORTHODONTIC APPLIANCE

(71) Applicant: Oxilio Ltd, Larnaca (CY)

(72) Inventor: Islam Khasanovich Raslambekov, Long Island City, NY (US)

(73) Assignee: Oxilio Ltd, Larnaca (CY)

( * ) Notice: Subject to any disclaimer, the term of this patent is extended or adjusted under 35 U.S.C. 154(b) by 0 days.

(21) Appl. No.: 17/366,304

(22) Filed: Jul. 2, 2021

(51) Int. Cl.
*G16H 20/40* (2018.01)
*A61C 7/00* (2006.01)
*G05B 19/4099* (2006.01)
*B29C 64/386* (2017.01)
*B33Y 50/00* (2015.01)

(52) U.S. Cl.
CPC ............. *G16H 20/40* (2018.01); *A61C 7/002* (2013.01); *B29C 64/386* (2017.08); *B33Y 50/00* (2014.12); *G05B 19/4099* (2013.01)

(58) Field of Classification Search
CPC .... G16H 20/40; G05B 19/4099; A61C 7/002; B29C 64/386; B33Y 50/00
See application file for complete search history.

(56) References Cited

U.S. PATENT DOCUMENTS

| | | | |
|---|---|---|---|
| 8,566,115 B2 | 10/2013 | Moore | |
| 9,703,798 B2 | 7/2017 | Srinivasan et al. | |
| 9,946,725 B1 | 4/2018 | Saviano et al. | |
| 10,204,112 B1 | 2/2019 | Bhargava et al. | |
| 10,504,198 B1 | 12/2019 | Ward | |
| 10,886,010 B2 * | 1/2021 | Arnone | G16H 70/60 |
| 10,993,782 B1 | 5/2021 | Raslambekov | |
| 2002/0172911 A1 * | 11/2002 | Cooper | A61C 7/00 433/24 |
| 2007/0071244 A1 * | 3/2007 | LaGasse | H04B 10/70 380/278 |
| 2007/0203743 A1 * | 8/2007 | Pfeiffer | G16H 40/20 705/2 |
| 2013/0151466 A1 | 6/2013 | Skaria et al. | |
| 2015/0019252 A1 * | 1/2015 | Dawson | G06Q 10/10 705/3 |

(Continued)

OTHER PUBLICATIONS

Vboxxcloud "Cloud Storage for Healthcare", retrieved on Feb. 18, 2021 (Feb. 18, 2021) from: https://vboxxcloud.com/healthcare-cloud.

(Continued)

*Primary Examiner* — Ronald D Hartman, Jr.
(74) *Attorney, Agent, or Firm* — BCF LLP

(57) ABSTRACT

A distributed computer system for manufacturing an orthodontic appliance for a subject is provided. The system comprises: a server communicatively couplable to electronic devices associated with sets of users, the sets of users comprising: a first set of users for providing preliminary orthodontic treatment plans for subjects, a second set of users for providing input to the preliminary orthodontic treatment plans, and a third set of users for manufacturing orthodontic appliances to implement at least a portion of finalized orthodontic treatment plans, the finalized orthodontic treatment plans being based on a given preliminary orthodontic treatment plan and a given input from a user of the second set of users to the given preliminary orthodontic treatment plan.

20 Claims, 10 Drawing Sheets

(56) References Cited

U.S. PATENT DOCUMENTS

| | | | | |
|---|---|---|---|---|
| 2015/0332018 A1* | 11/2015 | Rosen | ............... | G16H 10/40 |
| | | | | 705/2 |
| 2017/0083676 A1* | 3/2017 | Sigler | ............... | G16H 40/20 |
| 2018/0226157 A1 | 8/2018 | Blanshard et al. | | |
| 2019/0155789 A1 | 5/2019 | Dorman | | |
| 2019/0175303 A1* | 6/2019 | Akopov | ............... | A61C 7/08 |
| 2019/0197091 A1 | 6/2019 | Massand | | |
| 2019/0333622 A1* | 10/2019 | Levin | ............... | G06F 3/04845 |
| 2020/0066391 A1* | 2/2020 | Sachdeva | ............... | A61C 5/30 |
| 2021/0220086 A1* | 7/2021 | German | ............... | A61C 7/02 |
| 2021/0298874 A1* | 9/2021 | Katzman | ............... | G16H 20/00 |

OTHER PUBLICATIONS

Adler "Evaluating and implementing a collaborative office document system", published on Dec. 7, 2005, obtained on Feb. 19, 2019 from: https://citeseerx.ist.psu.edu/viewdoc/download?doi=10.1.1.923.8527&rep=rep1&type=pdf.
U.S. Appl. No. 17/143,074, filed Jan. 6, 2021.
U.S. Appl. No. 17/338,143, filed Jun. 3, 2021.
U.S. Appl. No. 16/704,718, filed Dec. 5, 2019.

* cited by examiner

SYSTEMS AND METHODS FOR MANUFACTURING AN ORTHODONTIC APPLIANCE

FIELD

The present technology relates generally to the field of orthodontics; and, in particular, to a distributed computer system for and a method of manufacturing an orthodontic appliance for a subject.

BACKGROUND

In orthodontics, treatments for achieving alignment of malposed teeth in a subject may include applying dental appliances causing subject's teeth to move to a desired position thereof, for example, that associated with their alignment. Planning the orthodontic treatment may typically include a number of health care professionals, potentially representing various entities and potentially located in different geographical locations.

One of such entities may be an orthodontic clinic where an operator may collect data pertaining to the orthodontic treatment of the subject, such as images of subject's arch forms, a medical history of the subject, and the like, for devising a preliminary orthodontic treatment plan. Generally, the orthodontic treatment may comprise a certain number of steps in which different orthodontic appliances are applied to the subject's teeth. Thus, the operator may further communicate certain parts of the preliminary orthodontic treatment plan, such as the arch form images corresponding to the steps of the treatment, to another entity (a laboratory, for example) for making the orthodontic appliances for providing them to the subject.

However, for various reasons, the preliminary orthodontic treatment plan may need to be revised during or between the treatment steps. This may be performed, for example, by the same or a different operator. In another example, the orthodontic treatment plan may be revised by a higher-level-skill orthodontic practitioner, such as an orthodontist or a maxillo-facial surgeon, for example, to improve the efficacy of the orthodontic treatment at a given step and/or reduce the discomfort caused to the subject after a first trial of the respective orthodontic appliance. By doing so, another version of the orthodontic treatment plan may be devised As it may be appreciated, when the above workflow is to be performed for many subjects or when the workflow for a given orthodontic treatment plan involves many operators and practitioners attending to the given orthodontic treatment plan at different steps thereof, a plurality of different versions of the given orthodontic treatment plan may be created, and can become easily confused. Furthermore, a given laboratory may collaborate with many different orthodontic practitioners. Working with the most up-to-date version of the given orthodontic treatment plan may become important. Working with out-dated versions may result in an ineffective treatment for the subject, not to mention wasted time and resources.

An example problematic situation is as follows: the operator creates the orthodontic treatment plan, uploading it into a computer system which the orthodontist can access through their private system account. The orthodontist may start editing the given orthodontic treatment plan, at the same time as the operator also edits it. In this situation, there may be a version conflict, resulting in a loss of the changes made by either or both ones of the operator and the orthodontist.

Certain prior art approaches have been proposed related to shared access to information relating the development of the orthodontic treatment plan at the computer system.

U.S. Pat. No. 9,946,725-1 issued on Apr. 17, 2018, assigned to Google LLC, and entitled "Systems and Methods for Incremental Loading of Collaboratively Generated Presentations" discloses systems and methods for incrementally communicating a document to a client computer. Time consistent views of the document are maintained throughout the incremental downloading through use of a cryptographically secured permissions token identifying a version of the document the user is permitted to access.

United States Patent Application Publication No.: 2019/155,789 published on May 23, 2019, assigned to Box Inc, and entitled "Method and Apparatus for Synchronization of Items with Read-only Permissions in a Cloud-based Environment" discloses techniques for enabling synchronization of items (e.g., folders or files) in a cloud-based environment. In one embodiment, a method comprises, upon receiving a request from a collaborator to synchronize an item stored in the workspace, verifying if the collaborator has permission for downloading the item. The method further comprises, if the collaborator has permission for downloading the item, sending the item to the collaborator. The method further comprises synchronizing the item by automatically pushing an updated version of the item unilaterally from the cloud-based environment to the collaborator regardless of whether the collaborator has performed any modification to the sent item. Among other advantages, embodiments disclosed herein provide capabilities to synchronize items in cloud-based platforms, especially where items are often opened/edited among the collaborators.

A web document entitled "Cloud Storage for Healthcare" placed by vBoxx at vboxxcloud.com/healthcare-cloud discloses a cloud-based collaborative environment with a capability of assigning rights to various users thereof and storing data for shared access.

U.S. Pat. No. 9,703,798-B2 issued on Jul. 11, 2017, assigned to CORALTREE Inc, and entitled "System and Method for File Sharing and Updating" discloses a method and system for sharing changes made by an application to a file on one computer, coherently with other computers, over the Internet. If the application changes multiple files (also referred to as a file group), changes made to all the files are shared together coherently with other computers over the Internet. Coherence over multiple file copies and file group copies is maintained whether users work on files online or offline. A 'File Upload Lock' is maintained on a Cloud Server for ensuring coherent sharing of changes made to files. Embodiments include two file syncing processes, variously described as 'Incremental File Upload' or 'Incremental File Download' and 'Delta File Upload' or 'Delta File Download'. Embodiments also encompass an 'Explorer' software tool and user interface that displays folders and files on user devices with pertinent details from the device and the Cloud Server.

United States Patent Application Publication No.: 2013/151,466-A1 published on Jun. 13, 2013, assigned to Microsoft Technology Licensing LLC, and entitled "Controlling Access to Documents Using File Locks" discloses systems and methods for controlling access to document files on a document server. One example system includes document files stored on a document server, at least one of the document files referencing a file lock, and a document access processing module. The example document access processing module includes a file sharing processing module that determines a coauthoring status of a software application of a client computer requesting access to the document file, and a file lock processing module that stores one or more file locks and that controls the setting and resetting of file locks. The example document access processing module uses the coauthoring status of the software application and the file lock status of a document file to determine whether a software application is permitted to have write access to the document file.

U.S. Pat. No. 8,566,115-B2 issued on Oct. 22, 2013, assigned to NewsILike Media Group Inc, and entitled "Syndicating Surgical Data in a Healthcare Environment" discloses systems and methods for syndication and management of structured and unstructured data to assist institutional healthcare delivery, healthcare providers' practices, healthcare providers' group practices, collaborative academic research and decision making in healthcare, including through the utilization of medical devices and healthcare pools.

U.S. Pat. No. 10,504,198-B1 issued on Dec. 10, 2019, assigned to REWARD HEALTH SCIENCES Inc, and entitled "Longitudinal Multi-author Care Planning and Management System with User-tailored Care Plan Hierarchy that Propagates based on Care Responsibility Information" discloses a method and system for care planning and management that provides a patient-centered single source of truth to foster teamwork and improved quality of care. The system facilitates creation of multi-author structured care plans through derivation of care relationships, care responsibilities and care plan elements to pre-populate care plans, and uses a hierarchical topic catalog and associated structured sentence templates and care plan templates to facilitate the completion of care plans. It aids interdisciplinary input through workflow-enabled routing of draft care plans, and rules-driven co-signing. The system allows each of multiple authors to separately tailor the sort order, hierarchy and information prominence of care plan structured sentences. The system uses care relationship and care responsibility information to optimize the propagation of care plan view tailoring instructions among co-authors. Finally, the system facilitates care plan execution using workflow automation technology to track and coordinate the process of delivering each ordered service.

U.S. Pat. No. 9,946,725-B1 issued on Apr. 17, 2018, assigned to Google Inc, and entitled "Systems and Methods for Incremental Loading of Collaboratively Generated Presentations" discloses systems and methods for incrementally communicating a document to a client computer. Time consistent views of the document are maintained throughout the incremental downloading through use of a cryptographically secured permissions token identifying a version of the document the user is permitted to access.

SUMMARY

It is an object of the present technology to ameliorate at least some of the inconveniences present in the prior art.

Developers of the present technology have devised a distributed computer system comprising a server communicatively couplable to workstations of the users involved in the process of development of the orthodontic treatment. More specifically, the developers have appreciated that a collaborative access to the orthodontic treatment may be more conveniently organized for all parties involved in the development thereof if the orthodontic treatment plan could be stored and modified solely on the server.

Further, to prevent conflicts between the versions of the orthodontic treatment plan created by different users, the server may be configured to implement certain restrictive policies allowing, for example, access only to one user at a time, subsequently restricting access to any other user. To that end, changes made by a given user (such as the orthodontist) working on the orthodontic treatment plan may be stored in a separate new version thereof. Additionally, at least one other user may be notified of the creation of the new version of the orthodontic treatment plan by the given user, and may thus attend to implementing their consecutive steps in the development of the orthodontic treatment plan.

The developers have also realized that computational burden on the server may be reduced if each new version of the orthodontic treatment plan is not created every time a respective previous version thereof is accessed by the given user, rather, by contrast, is created only if there have been changes made to the respective previous version of the orthodontic treatment plan. Such an approach may allow avoiding creating, storing, and transmitting unnecessary copies of the orthodontic treatment plan among the users, which may increase operational efficiency of the server.

Additionally, the developers have further appreciated that such an architecture of the computer system may allow saving changes made to the orthodontic treatment plan by certain users (for example, doctors) in a centralized manner for further predicting, for example, using a trained machine-learning algorithm, preferences of those particular users when automatically generating further orthodontic treatment plans associated with them. This may, for example, allow saving time on fine-tuning the orthodontic treatment plan by higher-level practitioners, which, in turn, increases efficiency of the orthodontic treatment plan development process.

Thus, in accordance with a first broad aspect of the present technology, there is provided a distributed computer system for manufacturing an orthodontic appliance for a subject. The system comprises: a server communicatively couplable to electronic devices associated with sets of users, a given electronic device configured to implement a thin client for accessing the server. The sets of users comprise: a first set of users for providing preliminary orthodontic treatment plans for subjects, a second set of users for providing input to the preliminary orthodontic treatment plans, and a third set of users for manufacturing orthodontic appliances to implement at least a portion of finalized orthodontic treatment plans, the finalized orthodontic treatment plans being based on a given preliminary orthodontic treatment plan and a given input from a user of the second set of users to the given preliminary orthodontic treatment plan. The server has a processor configured to execute a method, which comprises, for a given subject: accessing a preliminary digital orthodontic treatment plan for the given subject from a first electronic device associated with a first user of the first set of users; preventing access, to the preliminary digital orthodontic treatment plan during the accessing, by electronic devices associated with other users of the first set of users, all users of the second set of users, and all users of the third set of users; storing the preliminary digital orthodontic treatment plan in a memory of the server; on receipt of a request to access the stored preliminary digital orthodontic treatment plan from any user of the first set of users, second set of users and third set of users, accessing a predetermined rule of access, and determining a next user of the first set of users, second set of users and third set of users to provide access to the stored preliminary digital orthodontic treatment plan; providing access to an electronic device of the determined next user, a copy of the preliminary digital orthodontic treatment plan whilst retaining the preliminary digital orthodontic treatment plan in the memory; determining whether changes have been made to the copy of the preliminary digital orthodontic treatment plan by applying a hash function to a meta data structure of the copy of the preliminary digital orthodontic treatment plan, and if changes have been made to the copy of the preliminary digital orthodontic treatment plan, saving those changes in the memory as a new version of the preliminary digital orthodontic treatment plan; obtaining input regarding the saved new version of the preliminary digital orthodontic treatment plan being a given finalized orthodontic treatment plan, and providing access to a given user of the third set of users to the given finalized orthodontic treatment plan for manufacturing the orthodontic appliance according to at least a portion of the given finalized orthodontic treatment plan.

In some implementations of the distributed computer system, the hash function comprises a sum of md5 hashes.

In some implementations of the distributed computer system, the processor is further configured to prevent access, to the copy of the preliminary digital orthodontic treatment plan whilst the next user has access to the copy of the preliminary digital orthodontic treatment plan, by electronic devices associated with other users of the first set of users, the second set of users, and the third set of users.

In some implementations of the distributed computer system, after the new version of the preliminary digital orthodontic treatment plan is saved, on receipt of a request to access the preliminary digital orthodontic treatment plan from another given user of the first set of users, the second set of users and the third set of users, accessing the predetermined rule of access, and determining a next other user to provide access to the saved new version of the preliminary digital orthodontic treatment plan.

In some implementations of the distributed computer system, the processor is further configured, for a given user of the second set of users, to apply a trained machine learning algorithm to provide suggested inputs to the preliminary orthodontic treatment plan according to preferences of the given user.

In some implementations of the distributed computer system, the processor is configured to train a machine learning algorithm on orthodontic treatment plan preferences of a given user of the second set of users for providing suggested inputs to preliminary orthodontic treatment plans according to those preferences.

In some implementations of the distributed computer system, the second set of users are orthodontic dentists or doctors.

In some implementations of the distributed computer system, certain users may be associated with more than one of the first set of users, second set of users and third set of users.

In accordance with a second broad aspect of the present technology, there is provided a server for manufacturing an orthodontic appliance for a subject. The server is communicatively couplable to electronic devices associated with sets of users. A given electronic device is configured to implement a thin client for accessing the server. The sets of users comprise: a first set of users for providing preliminary orthodontic treatment plans for subjects, a second set of users for providing input to the preliminary orthodontic treatment plans, and a third set of users for manufacturing orthodontic appliances to implement at least a portion of finalized orthodontic treatment plans, the finalized orthodontic treatment plans being based on a given preliminary orthodontic treatment plan and a given input from a user of the second set of users to the given preliminary orthodontic treatment plan. The server includes: a processor and a non-transitory memory storing instructions. The processor, upon executing the instructions, is configured to: provide access to a preliminary digital orthodontic treatment plan for a given subject by a first electronic device associated with a first user of the first set of users; while providing access to the preliminary digital orthodontic treatment plan by the first electronic device, prevent access to the preliminary digital orthodontic treatment plan by electronic devices associated with other users of the first set of users, all users of the second set of users, and all users of the third set of users; store the preliminary digital orthodontic treatment plan in the non-transitory memory; on receipt of a request to access the stored preliminary digital orthodontic treatment plan from any user of the first set of users, second set of users and third set of users, access a predetermined rule of access to determine a next user of the first set of users, second set of users and third set of users to provide access to the stored preliminary digital orthodontic treatment plan; provide access to a copy of the preliminary digital orthodontic treatment plan by an electronic device of the determined next user, whilst retaining the preliminary digital orthodontic treatment plan in the non-transitory memory; determine whether changes have been made to the copy of the preliminary digital orthodontic treatment plan by applying a hash function to a meta data structure of the copy of the preliminary digital orthodontic treatment plan, and if changes have been made to the copy of the preliminary digital orthodontic treatment plan, save the changes in the non-transitory memory as a new version of the preliminary digital orthodontic treatment plan; obtain input regarding the saved new version of the preliminary digital orthodontic treatment plan being a given finalized orthodontic treatment plan and provide access to a given user of the third set of users to the given finalized orthodontic treatment plan for manufacturing the orthodontic appliance according to at least a portion of the given finalized orthodontic treatment plan.

In some implementations of the server, the processor is further configured to prevent access, to the copy of the preliminary digital orthodontic treatment plan whilst the determined next user has access to the copy of the preliminary digital orthodontic treatment plan, by electronic devices associated with other users of the first set of users, the second set of users, and the third set of users.

In some implementations of the server, after the new version of the preliminary digital orthodontic treatment plan is saved, on receipt of a request to access the preliminary digital orthodontic treatment plan from another given user of the first set of users, the second set of users and the third set of users, the processor is further configured to access the predetermined rule of access to determine a next other user to provide access to the saved new version of the preliminary digital orthodontic treatment plan.

In some implementations of the server, for a given user of the second set of users, the processor is further configured to apply a trained machine learning algorithm to provide suggested inputs to the preliminary orthodontic treatment plan according to preferences of the given user.

In some implementations of the server, the processor is further configured to train a machine learning algorithm on orthodontic treatment plan preferences of a given user of the second set of users for providing suggested inputs to preliminary orthodontic treatment plans according to those preferences.

In accordance with a third broad aspect of the present technology, there is provided a method of manufacturing an orthodontic appliance for a subject. The method is executable by a server including a processor. The server is communicatively couplable to electronic devices associated with sets of users, a given electronic device being configured to implement a thin client for accessing the server. The sets of users comprise: a first set of users for providing preliminary orthodontic treatment plans for subjects, a second set of users for providing input to the preliminary orthodontic treatment plans, and a third set of users for manufacturing orthodontic appliances to implement at least a portion of finalized orthodontic treatment plans, the finalized orthodontic treatment plans being based on a given preliminary orthodontic treatment plan and a given input from a user of the second set of users to the given preliminary orthodontic treatment plan. The method, for a given subject, comprises: providing, by the processor, access to a preliminary digital orthodontic treatment plan for the given subject by a first electronic device associated with a first user of the first set of users; during the providing access by the first electronic device, preventing access, to the preliminary digital orthodontic treatment plan, by electronic devices associated with other users of the first set of users, all users of the second set of users, and all users of the third set of users; storing, by the processor, the preliminary digital orthodontic treatment plan in a memory of the server; on receipt of a request to access the stored preliminary digital orthodontic treatment plan from any user of the first set of users, second set of users and third set of users, accessing, by the processor, a predetermined rule of access to determine a next user of the first set of users, second set of users and third set of users to provide access to the stored preliminary digital orthodontic treatment plan; providing, by the processor, access to an electronic device of the determined next user, a copy of the preliminary digital orthodontic treatment plan whilst retaining the preliminary digital orthodontic treatment plan in the memory; determining, by the processor, whether changes have been made to the copy of the preliminary digital orthodontic treatment plan by applying a hash function to a meta data structure of the copy of the preliminary digital orthodontic treatment plan, and if changes have been made to the copy of the preliminary digital orthodontic treatment plan, saving those changes in the memory as a new version of the preliminary digital orthodontic treatment plan; obtaining, by the processor, input regarding the saved new version of the preliminary digital orthodontic treatment plan being a given finalized orthodontic treatment plan, and providing, by the processor, access to a given user of the third set of users to the given finalized orthodontic treatment plan for manufacturing the orthodontic appliance according to at least a portion of the given finalized orthodontic treatment plan.

In some implementations of the method, the hash function comprises a sum of md5 hashes.

In some implementations of the method, the method further comprises preventing, by the processor, access, to the copy of the preliminary digital orthodontic treatment plan whilst the next user has access to the copy of the preliminary digital orthodontic treatment plan, by electronic devices associated with other users of the first set of users, the second set of users, and the third set of users.

In some implementations of the method, after the new version of the preliminary digital orthodontic treatment plan is saved, on receipt of a request to access the preliminary digital orthodontic treatment plan from another given user of the first set of users, the second set of users and the third set of users, accessing, by the processor, the predetermined rule of access to determine a next other user to provide access to the saved new version of the preliminary digital orthodontic treatment plan.

In some implementations of the method, the method further comprises, for a given user of the second set of users, applying a trained machine learning algorithm to provide suggested inputs to the preliminary orthodontic treatment plan according to preferences of the given user.

In some implementations of the method, a given one of the second set of users is one of an orthodontist, a dentist, and a doctor.

In some implementations of the method, certain users may be associated with more than one of the first set of users, second set of users and third set of users.

In the context of the present specification, the term "orthodontic treatment" is broadly referred to as any type of medical intervention aimed at correcting malocclusions associated with the subject's teeth or moving the patient's teeth for any reason, including surgical and non-surgical manipulations, such as, but not limited to, using one or more of aligners, brackets, multi-strand wires, strips, retainers, and plates. Further, the orthodontic treatment, as referred to herein, may be determined manually by a professional practitioner (such as an orthodontist, a maxillofacial surgeon, for example), automatically by a specific software based on image data and input parameters associated with the subject, and/or a combination of manual and automatic.

Also, as used herein, determining the orthodontic treatment may include verification of an already determined orthodontic treatment, for example, by modelling an effect of the determined orthodontic treatment using respective 3D models (such as 3D meshes) of the subject's teeth. The verification may be conducted, for example, to ensure safety and effectiveness of the determined orthodontic treatment for the subject.

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

Figure 1:
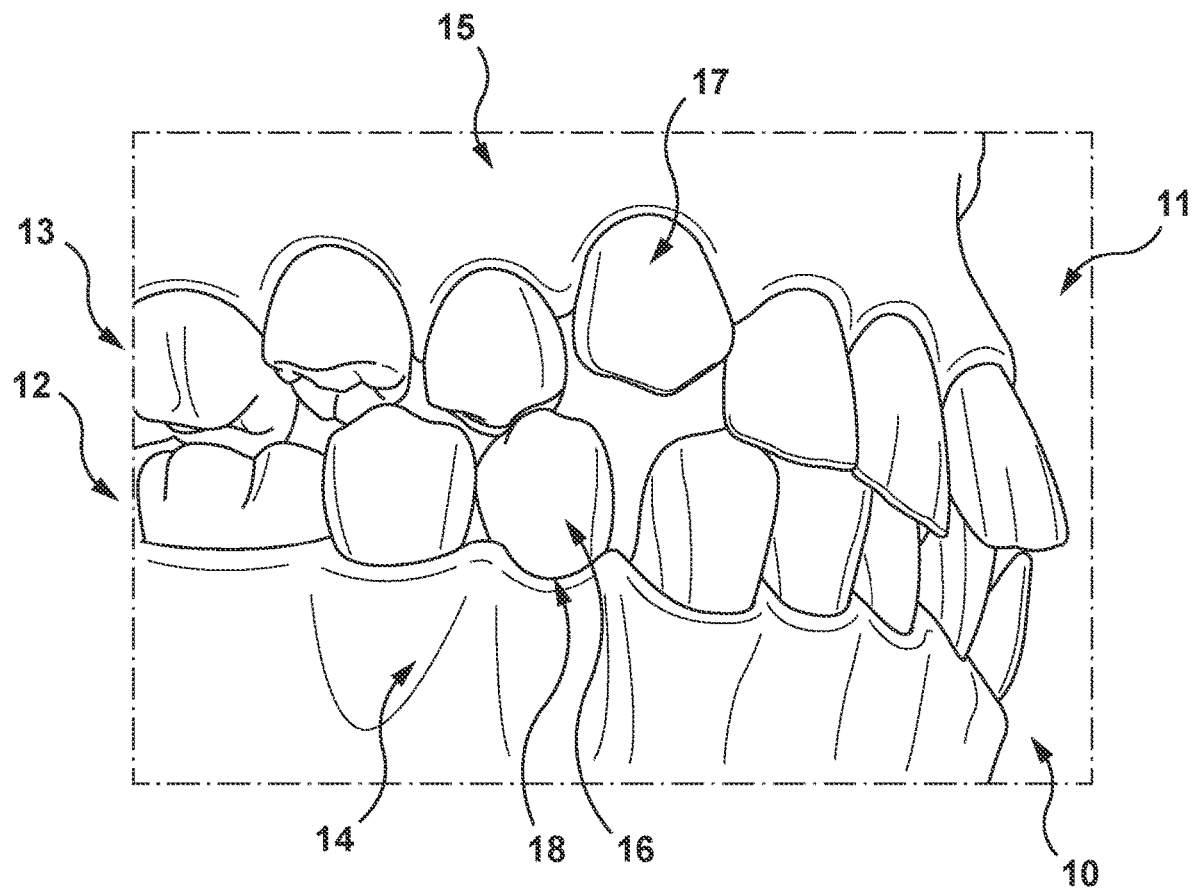
FIG. 1 depicts a perspective view of certain intraoral anatomical structures of a subject including a lower arch form and an upper arch form of the subject depicting examples of malocclusions of some of subject's teeth, in accordance with certain non-limiting embodiments of the present technology.

It should be noted that, unless otherwise explicitly specified herein, the drawings are not to scale.

DETAILED DESCRIPTION

Certain aspects and embodiments of the present technology are directed to methods of and systems for manufacturing an orthodontic appliance for a subject.

More specifically, certain aspects and embodiments of the present technology comprise a distributed computer system for executing a workflow of manufacturing the orthodontic appliance including determining an orthodontic treatment plan which may involve inputs from different entities and/or individuals, such as operators and orthodontic practitioners, for example. According to at least some non-limiting embodiments of the present technology, the distributed computer system may be configured to provide collaborative access to such entities and/or individuals to implement their steps in developing the orthodontic treatment plan avoiding conflicts of versions of the orthodontic treatment plan thereamong. This may be achieved, in some non-limiting embodiments of the present technology, by the distributed computer system being configured to provide the access to one of the entities and/or individuals at a time.

Certain embodiments of the present technology minimize, reduce or avoid some of the problems noted with the prior art. For example, by implementing certain embodiments of the present technology, efficiency of the manufacturing the orthodontic appliance may be increased.

For example, the efficiency of the manufacturing the orthodontic appliance can be increased via reducing computational resources of the distributed computer system on the developing the orthodontic treatment plan. For example, the reducing the computational resources may be achieved by the distributed computer system being configured to generate and save each new version of the orthodontic treatment plan only in case of changes made to a previous version of the orthodontic treatment plan—as opposed to generating each new version of orthodontic treatment plan every time it is accessed by an other entity and/or individual.

In another example, the efficiency of the manufacturing the orthodontic appliance can be increased through reducing the time spent on the developing the orthodontic treatment plan. In this regard, the reducing the time for the developing the orthodontic treatment plan may be achieved, according to certain non-limiting embodiments of the present technology, by saving changes to the orthodontic treatment in association with respective entities and/or individuals who have made those changes, which may be used for predicting, for example, by a specifically trained machine-learning algorithm, preferences of those entities and/or individuals when automatically generating further orthodontic treatment plans for other subjects. Such an approach to the automatic generation of orthodontic treatment plans may help save time on adjusting the orthodontic treatment plan by certain entities and/or individuals.

Orthodontic Treatment

With initial reference to FIG. 1, there is depicted a perspective view of a lower arch form 10 and an upper arch form 11 of the subject (not depicted), to which certain aspects and non-limiting embodiments of the present technology may be applied.

As can be appreciated, the lower arch form 10 includes lower teeth 12 and lower gingiva 14; and the upper arch form 11 includes upper teeth 13 and upper gingiva 15.

Further, in the depicted embodiments of FIG. 1, positions of at least some of the lower teeth 12 within the lower arch form 10 and those of the upper teeth 13 within the upper arch form 11 may be indicative of certain orthodontic disorders of the subject. For example, at least a given lower tooth 16 and a given upper tooth 17 are misaligned within a respective one of the lower arch form 10 and the upper arch form 11. Further, as the given lower tooth 16 is abnormally embedded within the lower teeth 12 while the given upper tooth 17 abnormally protrudes over opposing ones of the lower teeth 12, the misalignment thereof may affect the bite of the teeth, or, in other words, cause a malocclusion—that is, an irregular spatial relationship—between the lower teeth 12 and the upper teeth 13.

Other malocclusions (not depicted) associated with misalignment of lower teeth 12 relative to each other and the upper teeth 13, according to certain non-limiting embodiments of the present technology, may include, without limitation: overbites, underbites, crossbites, openbites, crowding of some of the lower teeth 12 and the upper teeth 13, midline shift therebetween, and others.

In some non-limiting embodiments of the present technology, for resolving the above-mentioned malocclusions, an orthodontic treatment may be provided to the subject.

In some non-limiting embodiments of the present technology, the orthodontic treatment may comprise applying an orthodontic appliance to the subject's teeth. Generally speaking, the orthodontic appliance may be configured to exert a respective predetermined force onto at least some of the lower teeth 12 and the upper teeth 13—such as the given lower tooth 16 and the given upper tooth 17, causing them to move towards an aligned position, thereby restoring the normal occlusion of the lower teeth 12 relative to upper teeth 13 of the subject. More specifically, in the depicted embodiments of FIG. 1, the orthodontic appliance may be configured to cause the given lower tooth 16 to move outwardly between lower teeth adjacent thereto; and further cause clockwise rotation thereof. Further, the orthodontic appliance may be configured to cause the given upper tooth 17 to move inwardly. In various non-limiting embodiments of the present technology, the orthodontic appliance may comprise orthodontic appliances of different types, shapes, sizes and configurations, such as those including, without limitation, aligners, brackets, multi-strand wires, strips, retainers, and plates.

In some non-limiting embodiments of the present technology, the orthodontic appliance may be selected, in the course of the orthodontic treatment to correct a respective malocclusion. For example, in some non-limiting embodiments of the present technology, the orthodontic appliance may include a biteplate (not depicted) used for correcting the overbites. More specifically, the biteplate may be configured for preventing front ones of upper teeth 13 overlap front ones of the lower teeth 12 for extended periods of time.

Further, in some non-limiting embodiments of the present technology, the orthodontic appliance may include a bitesplint (not depicted), which may be applied to the lower teeth 12 for correcting the crossbites—a lateral misalignment of one of the lower arch form 10 and the upper arch form 11 resulting, for example, in buccal surfaces of some of the upper teeth 13 overlapping lingual surfaces of opposing ones thereof of the lower teeth 12. To that end, the bitesplint may be configured for preventing the subject from biting completely, which may further allow correcting the crossbites.

Figure 2:
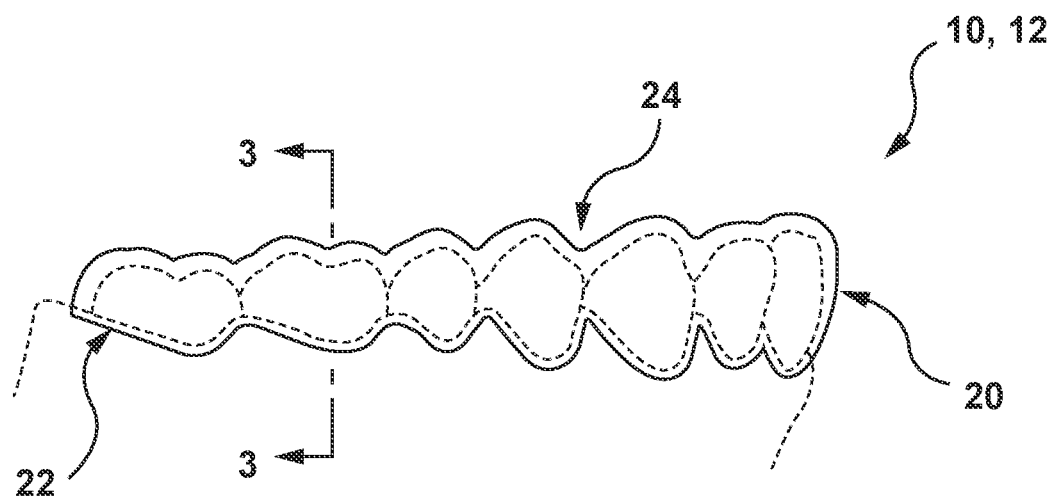
FIGS. 2 and 3 depict a side view and a cross-sectional view through line 3-3, respectively, of an orthodontic appliance applied to the subject's teeth that may be configured to treat the malocclusions of the subject's teeth present in FIG. 1, in accordance with certain non-limiting embodiments of the present technology.
Figure 3:
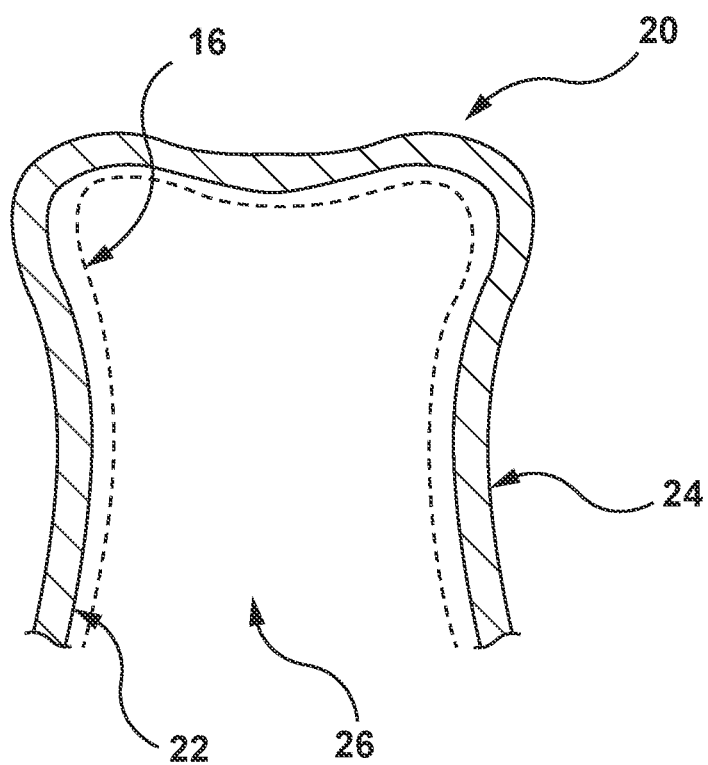

In specific non-limiting embodiments of the present the present technology, the orthodontic appliance may include at least one aligner. With reference to FIGS. 2 and 3, there is depicted an aligner 20 applied to at least some of the lower teeth 12, in accordance with certain non-limiting embodiments of the present technology. The aligner 20 comprises an inner surface 22 and an outer surface 24. The inner surface 22 defines a channel 26, which is configured, in some non-limiting embodiments of the present technology, for receiving crown portions of at least some of the lower teeth 12, such as the given lower tooth 16. However, in other non-limiting embodiments of the present technology, the channel 26 of the aligner 20 may be configured to receive crown portions of all of the lower teeth 12. At least one edge (also referred to herein as an "open edge") of the channel 26 is shaped for following a gum line (not depicted) along the lower gingiva 14.

It will be appreciated that, in accordance with certain non-limiting embodiments of the present technology, the aligner 20 may be used for treating different teeth malocclusions, including but not limited to one or more of: closing interdental spaces ("space closure"), creating/widening interdental spaces, tooth rotation, tooth intrusion/extrusion, and tooth translation, to name a few. It should further be noted that in certain non-limiting embodiments of the present technology, applying the aligner 20 to the lower teeth 12 may further include applying specific attachments thereto.

As may become apparent, the aligner 20 may be designed in such a way that its inner surface 22 is configured to impose respective forces on one or more of the lower teeth 12 to obtain a desired position of the lower teeth 12 at a given stage of the orthodontic treatment.

Needles to say that, although in the depicted embodiments of FIGS. 2 and 3, the aligner 20 is configured to be applied onto the lower teeth 12, in other non-limiting embodiments of the present technology, a respective configuration of the aligner 20 may be applied to the upper teeth 13 of the subject for treating misalignment of at least some thereof—such as the given upper tooth 17. By so doing, the desired occlusion between the lower teeth 12 and the upper teeth 13 may be attained.

According to certain non-limiting embodiments of the present technology, the aligner 20 may be made of a polymer, such as a thermoplastic material. In other non-limiting embodiments of the present technology, the aligner 20 may be made of poly-vinyl chloride (PVC). In yet other non-limiting embodiments of the present technology, the aligner 20 may be made of polyethylene terephthalate glycol (PETG). Other suitable materials can also be used to form the aligner 20.

In some non-limiting embodiments of the present technology, the aligner 20 may be manufactured using additive manufacturing techniques, such as 3D printing techniques where the aligner 20 is formed by printing according to a pre-generated 3D digital model thereof.

In other non-limiting embodiments of the present technology, the aligner 20 may be produced by a thermoforming process where (1) an unfinished aligner is produced, using a preform, on a respective aligner mold (not depicted) associated with a respective stage of the orthodontic treatment, which is configured to shape the inner surface 22 of the aligner 20; and (2) the unfinished aligner is cut along a predetermined cut line to remove excess material therefrom, thereby producing the aligner 20, the predetermined cut line defining the at least one edge of the channel 26 of the aligner 20.

In specific non-limiting embodiments of the present technology, the aligner 20 may be manufactured in accordance with one or more methods described in a co-owned U.S.

patent application Ser. No. 17/143,074 filed on Jan. 6, 2021, entitled "SYSTEMS AND METHODS FOR FORMING A DENTAL APPLIANCE," the content of which is incorporated herein by reference in its entirety.

As it may become apparent, to produce the aligner 20 for achieving the desired occlusal relationship between the lower teeth 12 and the upper teeth 13 during the orthodontic treatment, the tooth movements of the subject's teeth to which the aligner 20 is to be applied to should be carefully planned, based on respective 3D digital models (such as a 3D model 710 depicted in FIG. 7, for example) of the lower arch form 10 and the upper arch form 11, for example, to determine respective forces applied to the subject's teeth during respective stages of the orthodontic treatment. For example, the respective 3D digital models of each one of the lower arch form 10 and the upper arch form 11 of the subject may be generated using intra-oral scanning techniques.

Thus, as it can be appreciated the process for manufacturing the aligner 20 for the subject may involve certain steps that may be implemented by different entities (such as clinics and laboratories, for example) and/or users (such as operators, orthodontic practitioners of different levels, and the like). By way of example, (i) accessing current configurations of the lower arch form 10 and the upper arch form 11, for example, based on the respective 3D digital models, may be performed by an intermediary orthodontic practitioner (such as a dentist/orthodontist assistant, a dental/orthodontic nurse, for example). Further, the intermediary orthodontic practitioner may then communicate the respective 3D digital models to an entity running a specific digital treatment planning application for (ii) determining a preliminary version of the orthodontic treatment plan. In some cases, the preliminary version of the orthodontic treatment plan may further need to be (iii) reviewed by a higher-level orthodontic practitioner (for example, a dentist, an orthodontist, a maxillo-facial surgeon, and the like), who can further communicate the finalized orthodontic treatment plan for (iv) to the subject for presentation of the finalized orthodontic treatment plan thereto and (v) to a laboratory facility for the manufacturing at least one configuration of the aligner 20 for implementing the orthodontic treatment.

As it can further be appreciated, the structure of such a workflow for the manufacturing the aligner 20 may permit at least some of the above-mentioned users involved therein to work on the orthodontic treatment plan simultaneously, which may cause loss of changes made by at least some of these users further resulting in an ineffective orthodontic treatment, damage to the subject's teeth, not to mention, wasted time and resources for implementing such a faulty orthodontic treatment plan.

Thus, to address the above-identified technical problem, non-limiting embodiments of a distributed computer system described herein has been developed. More specifically, the distributed computer system includes a server communicatively couplable to electronic devices of the users involved in the process of the manufacturing the aligner 20. According to certain non-limiting embodiments of the present technology, the server may be configured to host a current version of the orthodontic treatment plan providing collaborative access, through a respective electronic device, to each one of the users.

Such an architecture of the distributed computer system may allow to implement certain restrictive policies on the server to prevent access to the orthodontic treatment plan to any of the users while a given one thereof is working on the orthodontic treatment plan. Accordingly, such an approach to providing the collaborative access to the orthodontic treatment plan may eliminate any chances of version conflicts, thereby improving effectiveness and efficiency of the process for the manufacturing the aligner 20 and those of the orthodontic treatment itself.

Further, the efficiency of the process for the manufacturing the aligner 20 may further be increased by saving computational resources of the distributed computer system on unnecessary data transmission by saving only versions of the orthodontic treatment plan including actual changes made thereto, and not creating new versions solely in response to accessing the current version by another user.

In this regard, the architecture of the distributed computer system described herein allows accumulating, on the server, changes made by particular users and further take those changes into account when automatically generating further orthodontic treatment plans associated with those particular users, which may save time on adjusting the finalized treatment plan and thus translate in even higher efficiency of the process for the manufacturing the aligner 20.

The architecture of the distributed computer system and communication among different types of users therewithin will be described in greater detail with reference to FIGS. 4 to 9.

Computing Environment

Figure 4:
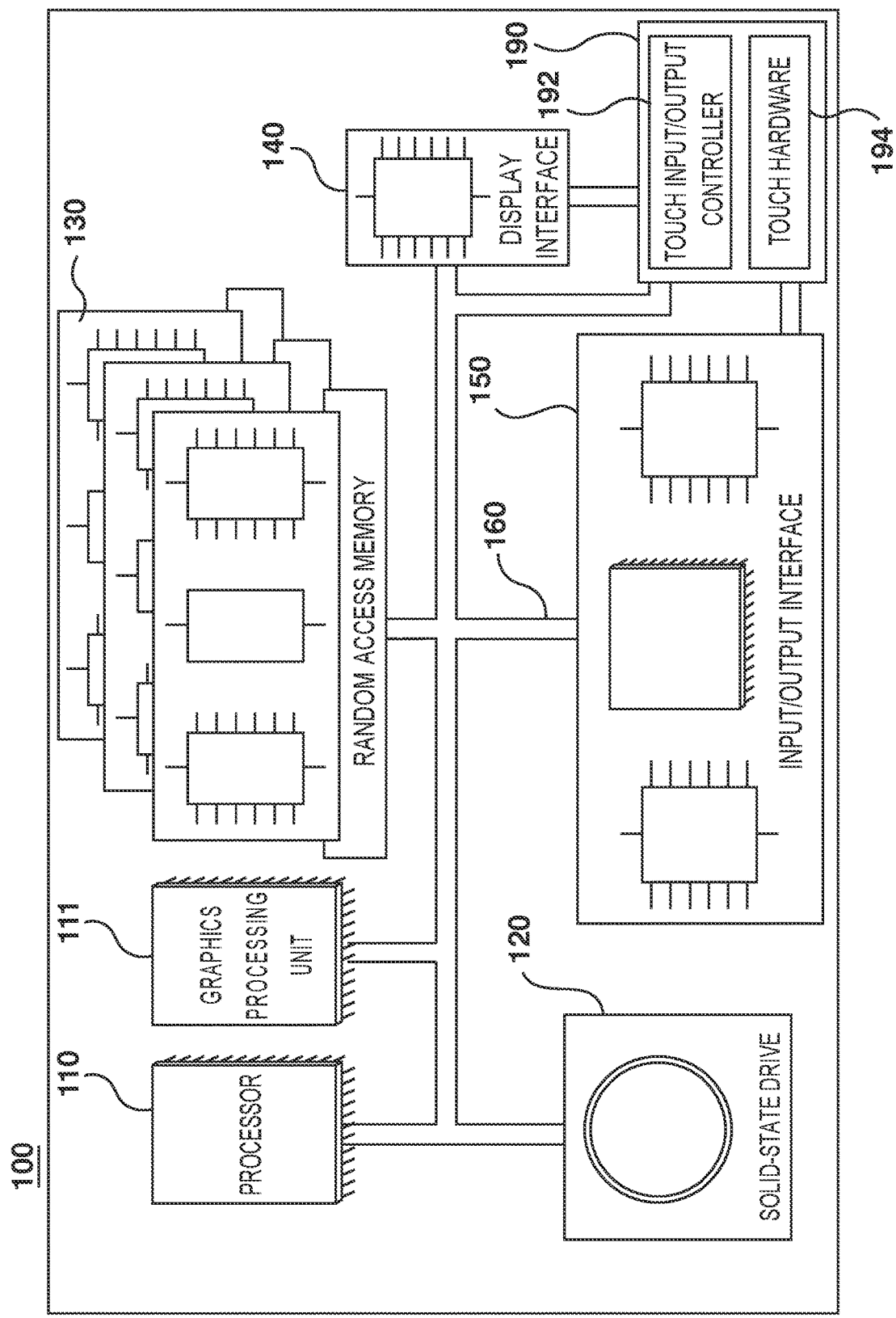
FIG. 4 depicts a schematic diagram of an example computing environment suitable for implementing certain non-limiting embodiments of systems and/or methods of the present technology.

With reference to FIG. 4, there is depicted a computing environment 100 suitable for use with some implementations of the present technology, in accordance with certain non-limiting embodiments of the present technology. The computing environment 100 comprises various hardware components including one or more single or multi-core processors collectively represented by a processor 110, a graphics processing unit (GPU) 111, a solid-state drive 120, a random-access memory 130, a display interface 140, and an input/output interface 150.

Communication between the various components of the computing environment 100 may be enabled by one or more internal and/or external buses 160 (e.g. a Peripheral Component Interconnect (PCI) bus, universal serial bus (USB), IEEE 1394 "Firewire" bus, a Small Computer System Interface (SCSI) bus, a Serial-AT-Attachment (SATA) bus, etc.), to which the various hardware components are electronically coupled.

The input/output interface 150 may be coupled to a touchscreen 190 and/or to the one or more internal and/or external buses 160. The touchscreen 190 may be part of the display. In some embodiments, the touchscreen 190 is the display. The touchscreen 190 may equally be referred to as a screen 190. In the embodiments illustrated in FIG. 1, the touchscreen 190 comprises touch hardware 194 (e.g., pressure-sensitive cells embedded in a layer of a display allowing detection of a physical interaction between a user and the display) and a touch input/output controller 192 allowing communication with the display interface 140 and/or the one or more internal and/or external buses 160. In some non-limiting embodiments of the present technology, the input/output interface 150 may be connected to a keyboard (not shown), a mouse (not shown) or a trackpad (not shown) allowing the user to interact with the computing environment 100 in addition to or instead of the touchscreen 190. In some embodiments, the computing environment 100 may comprise one or more microphones (not shown). The microphones may record audio, such as user utterances. The user utterances may be translated to commands for controlling the computing environment 100.

It is noted some components of the computing environment 100 can be omitted in some non-limiting embodiments of the present technology. For example, the touchscreen 190 can be omitted, especially (but not limited to) where the computing environment is implemented as a smart speaker device.

According to implementations of the present technology, the solid-state drive 120 stores program instructions suitable for being loaded into the random-access memory 130 and executed by the processor 110 and/or the GPU 111. For example, the program instructions may be part of a library or an application.

System

Figure 5:
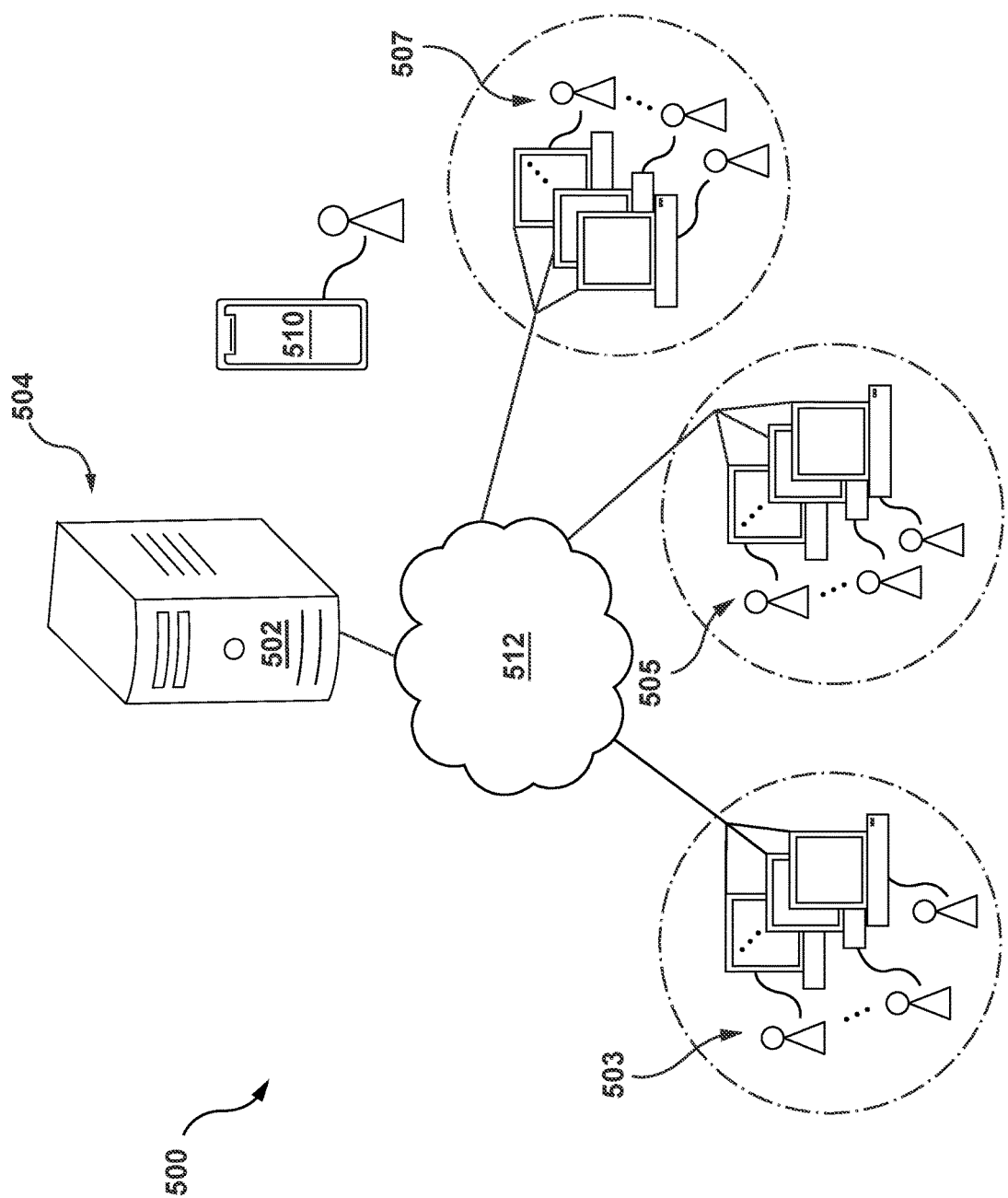
FIG. 5 depicts a schematic diagram of a distributed computer system for manufacturing the orthodontic appliance of FIGS. 2 and 3 for treating the malocclusions depicted in FIG. 1, in accordance with certain embodiments of the present technology.

With reference to FIG. 5, there is depicted a schematic diagram of a distributed computer system 500 for manufacturing an orthodontic appliance (such as the aligner 20), in accordance with certain non-limiting embodiments of the present technology. The distributed computer system 500 comprises a server 502 communicatively coupled, via a communication network 512, to production electronic devices (not separately numbered) of various users involved in the process of manufacturing the aligner 20, such as a first set of users 503, a second set of users 505, and a third set of users 507.

In some non-limiting embodiments of the present technology, the server 502 is implemented as a conventional computer server and may comprise some or all of the components of the computer system 100 of FIG. 4. In a specific non-limiting example, the server 502 is implemented as a Dell™ PowerEdge™ Server running the Microsoft™ Windows Server™ operating system, but can also be implemented in any other suitable hardware, software, and/or firmware, or a combination thereof. In the depicted non-limiting embodiments of the present technology, the server 502 is a single server. In alternative non-limiting embodiments of the present technology (not depicted), the functionality of the server 502 may be distributed and may be implemented via multiple servers.

Further, according to certain non-limiting embodiments of the present technology, each one of the production electronic devices of the first set of users 503, the second set of users 505, and the third set of users 507 can be any computer hardware that is capable of running a software appropriate to the relevant task at hand. To that end, each one of the production electronic devices may include some or all of the components of the computer system 100 of FIG. 4. More specifically, some non-limiting examples of the production electronic devices may include personal computers (desktops, laptops, netbooks, etc.), smartphones, tablets, and the like.

Also communicatively coupled to the server 502 is a patient electronic device 510 of the subject (not separately labelled in FIG. 5). As it can be appreciated, the patient electronic device 510 can be implemented in a similar fashion to one of the production electronic devices; and may thus comprise some or all components of the computing environment 100 of FIG. 4.

According to certain non-limiting embodiments of the present technology, the server 502 can be configured to run a digital treatment planning application 504. Broadly speaking, the digital treatment application 504 can be configured for generating the orthodontic treatment plan for the subject based on subject's data. The subject's data may include, without limitation, image data pertaining to the subject's intraoral anatomy, such as the respective 3D digital models (such as a 3D digital model 810 depicted in FIG. 7) of the lower arch form 10 and the lower arch form 11, anthropometric parameters associated with the subject, their medical history, and the like. Also, the digital treatment planning application 504 can provide functionality for viewing and modifying already generated orthodontic treatment plans to generate different versions thereof, as will be described below.

In some non-limiting embodiments of the present technology, the digital treatment planning application 504 can be a client-server application, thereby enabling the server 502 to store a current version of the orthodontic treatment plan of the subject and provide a collaborative access thereto to each one of the first set of users 503, the second set of users 505, and the third set of users 507, via respective production electronic devices thereof, which, in turn, can be configured to run a client version of the digital treatment planning application 504.

In specific non-limiting embodiments of the present technology, the digital treatment planning application 504 can be a thin-client application with most of its functionality being executed on the server 502 and providing only a respective user interface to each one of the first set of users 503, the second set of users 505, the third set of users 507, and the subject, for example, via a browser application of each one of their production electronic devices.

To that end, in some non-limiting embodiments of the present technology, each one of the first set of users 503, the second set of users 505, the third set of users 507, and the subject may have a respective user account with the digital treatment planning application 504 providing them with access to the current version of the orthodontic treatment plan from their electronic devices. For example, to log in in their respective user account of digital treatment planning application 504 from their electronic device, a given user may use a unique predetermined set of credentials (such as login and password) associated therewith, which they may enter in a login page (not depicted) of the digital treatment planning application 504 accessible using the browser application.

In a specific non-limiting example, the digital treatment planning application 504 may be a Vision™ digital treatment planning application provided by SOFTSMILE INC. of 197 NJ-18 #3000, East Brunswick, N.J. 08816, United States. It should be expressly understood that other suitable software applications for planning orthodontic treatments can be used without departing from the scope of the present technology.

Thus, the server 502 can be configured to manufacture the aligner 20 based on inputs provided by representatives of each one of the first set of users 503, the second set of users 505, and the third set of users 507. For example, in some non-limiting embodiments of the present technology, a given one of the first set of user 503, using a respective production electronic device thereof, may access and submit, via the digital treatment planning application 504, the subject's data to the server 502 to generate a preliminary version of the orthodontic treatment plan for the subject. In this regard, the first set of users 503 may include, for example, low- and middle-level medical practitioners, such as orthodontic/dental nurses or orthodontist/dentist assistants.

Further, in some non-limiting embodiments of the present technology, a given one of the second set of users 505 may review and modify, via the digital treatment planning application 504, the so generated preliminary version of orthodontic treatment plan provided by the first set of users 503 to generate a finalized version of the orthodontic treatment plan for the subject. For example, the given one of the second set of users 505 may be a higher-level medical practitioner, such as, without limitations, a medical doctor, a dentist, an orthodontist, a maxillo-facial surgeon, and the like. The so generated finalized version of the orthodontic treatment may further be stored as a current version thereof on the server 502.

Finally, a given one of the third set of users 507 can access the current version of the orthodontic treatment plan for manufacturing, in accordance therewith, at least one configuration of the aligner 20 for implementing the orthodontic treatment. As it can be appreciated, the given one of the third set of users 507 can, for example, be an operator of a laboratory for producing orthodontic appliances based on provided orthodontic treatment plans.

Access Distribution

In some non-limiting embodiments of the present technology, the server 502 could be configured to provide access to each one of the first set of users 503, the second set of users 505, the third set of users, and the subject based on a respective request received from their electronic devices. For example, once the given user, using their unique predetermined set of credentials, has logged in their user account with the digital treatment planning application 504 as described above, the server 502 can be configured to provide them with a dedicated interface for accessing one or more orthodontic treatment plans available for access.

Figure 6:
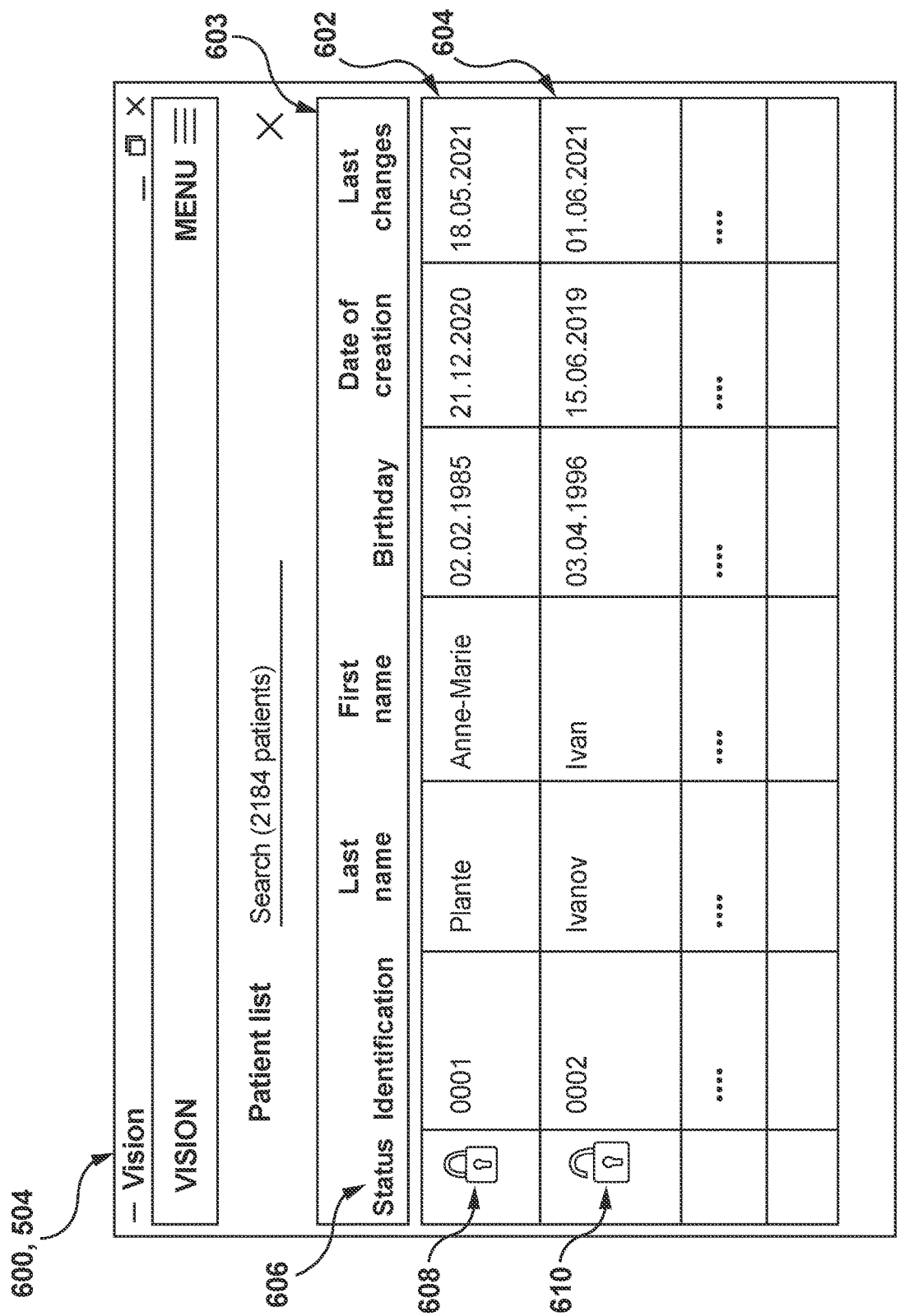
FIG. 6 depicts an example interface of a digital treatment planning application run at the server of the distributed computer system of FIG. 5 and used for collaborative access to one or more orthodontic treatment plans, in accordance with certain non-limiting embodiments of the present technology.

With reference to FIG. 6, there is depicted an example of a patient list interface 600 of the digital treatment planning application 504, in accordance with certain non-limiting embodiments of the present technology. As it can be appreciated, the patient list interface 600 can include a plurality of records corresponding to currently developed orthodontic treatment plans—such as a first record 602 corresponding to a first orthodontic treatment plan of a first subject and a second record 604 corresponding to a second orthodontic treatment plan of a second subject. Accordingly, by selecting (such as by clicking on) a given one of the first record 1002 and the second record 1004 in the patient list interface 1000, from a respective electronic device, the given user may generate a request to access a respective one of the first and second orthodontic treatment plans. In response, the server 502 could be configured to either grant or prevent access to the given user to the respective orthodontic treatment plan in another interface (such as a setup interface 800 described below with reference to FIG. 8) of the digital treatment plan application 504 allowing, for example, reviewing and/or modifying the respective orthodontic treatment plan, as will be described below.

According to certain non-limiting embodiments of the present technology, the patient list interface 600 may include a plurality of predetermined fields 603, each of which is indicative of a respective piece of data associated with the respective orthodontic treatment plan, such as an identification number, first and last names of subjects, their birthdays, and the like. Although in the depicted embodiments, the plurality of predetermined fields 603 includes seven fields, it should be expressly understood that in other non-limiting embodiments of the present technology, the plurality of predetermined fields 603, depending on preferences set in the digital treatment planning application 504 by the given user, may include more predetermined fields, such as, without limitation, 'Subject's diagnosis', 'Subject's time zone', and the like.

Further, in some non-limiting embodiments of the present technology, the plurality of predetermined fields 603 may include a status filed 606. According to certain non-limiting embodiments of the present technology, a respective value of the status field 606 is indicative of whether the respective orthodontic treatment plan is accessible by a respective electronic device of (or otherwise under a respective user account of) the given user of the digital treatment planning application 504 or not. In some non-limiting embodiments of the present technology, the respective value of the status field 606 may be binary. For example, the current version of the first orthodontic treatment plan may be currently checked by an other user; to that end, the server 502 can be configured to assign a positive value of the status field 606 in the first record 602, which can be indicated by a first icon 608 (closed lock). By doing so, the server 502 is configured to restrict access to the current version of the first orthodontic treatment plan by the respective electronic device of the given user of the digital treatment planning application 504 for modifications. Further, in response to selecting (such as by clicking on), by the given user, the first record 602 having the positive value of the status field 606, the server 502 could be configured not to open the first orthodontic treatment plan in the setup interface 800. For example, in some non-limiting embodiments of the present technology, by assigning the positive value to the status filed 606 in the first record 602, the server 502 can be configured to render the first field 602 non-selectable (non-clickable), such as greyed out. In additional non-limiting embodiments of the present technology, the server 502 can further be configured to generate a pop-up message (not depicted), such as "The selected orthodontic treatment plan is currently checked by another user. Please try again later", informing the given user of the unavailability of the first orthodontic treatment plan.

Additionally or alternatively, when the first record 602 has the positive value of the status field 606, the server 502 may be configured to provide access to the first orthodontic treatment plan, however, in a "read only" mode, that is, allowing the given user only to review the current version of the first orthodontic treatment plan in the setup interface 800 of the digital treatment planning application 504, while disabling therein any functionality for making changes.

In another example, the current version of the second orthodontic treatment plan could be currently not checked by any other user; and as such the server 502 can be configured to assign therein a negative value of the status field 606, which can be represented by a second icon 610 (open lock). Thus, in response to selecting (such as by clicking on), by the given user, the second record 602 having the negative value of the status field 606, the server 502 could be configured to grant the respective request for access to the second orthodontic treatment plan and open it in the setup interface 800 allowing the given user further modifications of the second orthodontic treatment plan, as will be described below. To that end, as will be described in greater detail below, the server 502 can be configured to transmit to the respective electronic device of the given user at least some data indicative of the current version of the second orthodontic treatment plan for presentation thereof to the given user.

In some non-limiting embodiments of the present technology, the server 502 can be configured to set up, via the digital treatment planning application 504, certain predetermined rules (such as restrictive policies) of access to the current version of the orthodontic treatment plan defining how the current version of the orthodontic treatment plan may be accessed by each one of the first set of users 503, the second set of users 505, the third set of users 507, and the subject. For example, in some non-limiting embodiments of the present technology, a given predetermined rule of access may allow accessing the current version of the orthodontic treatment plan by whomever is first to access it.

However, in other non-limiting embodiments of the present technology, the given predetermined rule of access to the current version of the orthodontic treatment plan may define a sequence of access thereto among the given one of the first set of users 503, the given one of the second set of users 505, and the given one of the third set of users 507. For example, the server 502 may be configured to allow accessing the current version of the orthodontic treatment plan, sequentially, first, by the given one of the first set of users 503; second, by the given one of the second set of users 505, and only then by the given one of the third set of users 507.

More specifically, as will be described in greater detail below, the given one of the first set of users 503 may create the predetermined version of the orthodontic treatment plan; and an indication thereof can further be generated in the patient list interface 600 of the digital treatment planning application 504, as described above. Further, the given one of the third set of users 507, via a respective production electronic device, may be able to see a respective record corresponding to the orthodontic treatment plan, and generate the respective request to the server 502 for access to the orthodontic treatment plan for further manufacturing at least one configuration of the aligner 20 in accordance therewith.

However, as the preliminary version of the orthodontic treatment plan has not yet been reviewed by the given one of the second set of users 505, the server 502 can be configured to prevent access to the orthodontic treatment plan from the respective production electronic device of the given one of the third set of users 507, by inactivating the respective record associated therewith in the patient list interface 600 (similar to the first record 602 described above) when opened under a user account of the given one of the third set of users 507. Further, once the given one of the second set of users 505 has reviewed and revised the preliminary version of the orthodontic treatment plan, thereby creating the finalized version thereof, the respective record associated with the orthodontic treatment plan in the patient list interface 600 may thus become available for access (similar to the second record 604) by the given one of the third set of users 507.

In other words, the given predetermined rule of access may allow the given one of the third set of users 507 to access only the finalized version of the orthodontic treatment plan. In this regard, to implement the given predetermined rule of access, in some non-limiting embodiments of the present technology, the status field 606 of the patient list interface 600 may have multiple values. By way of example, and not as a limitation, once the predetermined version has been generated, the server 502 can be configured to assign a first value of the status field 606 in the respective record corresponding to the orthodontic treatment plan, which may be indicated by an icon "Pending approval" (not depicted). To that end, the first value of the status filed 606 may be to inactivate the respective record under the user account of the given one of the third set of users 507, however, make it available under a user account of the given one of the second set of users 505.

In another example, once the given one of the second set of users 505 has created the finalized version of the orthodontic treatment plan, the server 502 can be configured to assign a second value to the status field 606 in the respective record corresponding to the orthodontic treatment plan, which may be for still preventing access from the user account of the given one of the third set of users 507 as the server 502 may, for example, await an input from the subject. To that end, the second value of the status filed 606 may be indicated by one of the following icons (not depicted): "Sent to the client", "Waiting for payment", and the like.

In yet another example, once the server 502 has received the input from the patient electronic device 510 of the subject, the server 502 could further be configured to assign a third value to the status field 606 in the respective record corresponding to the orthodontic treatment plan, thereby allowing access thereto from the user account of the given one of the third set of users 507. To that end, the third value of the status filed 606 may be indicated, in the respective record of the patient list interface 600 corresponding to the orthodontic treatment plan, by one of the following icons (not depicted): "Payment received", "Ready for manufacture", and the like. In additional non-limiting embodiments of the present technology, based on the given predetermined rule of access, the server 502 can be configured to proactively request, at each stage of the process for the manufacturing the aligner 20, that the respective users access the current version of the orthodontic treatment plan for introducing their inputs thereto. For example, the server 502 could be configured to send notifications (for example, by email) to the respective users when their inputs are required.

It should be expressly understood that a number of multiple values of the status field 606 is not limited and, in various non-limiting embodiments of the present technology, the status field 606 may have more than three values described above, which may thus be indicated by different respective icons, some of which will be described below.

It should further be noted that other permissions and restrictions defined by the given predetermined rule of access can also be envisioned without departing from the scope of the present technology. In one example, the given predetermined rule may further prioritize requests submitted by one users, such as the given one of the second set of users 505, concurrently with requests from other users. In another example, the given predetermined rule may further be for aborting access to the current version of the orthodontic treatment plan to any user if a prioritized request has been received and further grant the prioritized request. In yet another example, the given predetermined rule may further grant access to some of the users, such as the given one of the second set of users 505, at any stage of the manufacturing the aligner 20.

Thus, the given predetermined rule of access may be configured to define availability of certain functions in the patient list interface 600 of the digital treatment planning application 504 run under each respective user account of the first set of users 503, the second set of user 505, the third set of users 507, and the subject, thereby controlling access by each of them to the current version of the orthodontic treatment plan from their respective electronic devices.

How communication among the first set of users 503, the second set of users 505, and the third set of users 507 within the distributed computer system 500 can be organized for manufacturing the aligner 20 will be described in greater detail with reference to FIGS. 6, 8, and 9.

Communication Network

In some non-limiting embodiments of the present technology, the communication network 512 is the Internet. In alternative non-limiting embodiments of the present technology, the communication network 512 can be implemented as any suitable local area network (LAN), wide area network (WAN), a private communication network or the like. It should be expressly understood that implementations for the communication network 512 are for illustration purposes only. How a respective communication link (not separately numbered) between each one of the server 502, each one of the production electronic devices of the first set of users 503, the second set of users 505, and the third set of users 507, as well as the patient electronic device 510 and the communication network 512 is implemented will depend, inter alia, on how each one of the server 502, each one of the production electronic devices, and the patient electronic device 510 is implemented. Merely as an example and not as a limitation, in those embodiments of the present technology where the patient electronic device 510 is implemented as a wireless communication device such as a smartphone, the communication link can be implemented as a wireless communication link. Examples of wireless communication links include, but are not limited to, a 3G communication network link, a 4G communication network link, and the like. The communication network 512 may also use a wireless connection with the server 502 and at least some of the production electronic devices.

Generation of a Preliminary Orthodontic Treatment Plan

Figure 7:
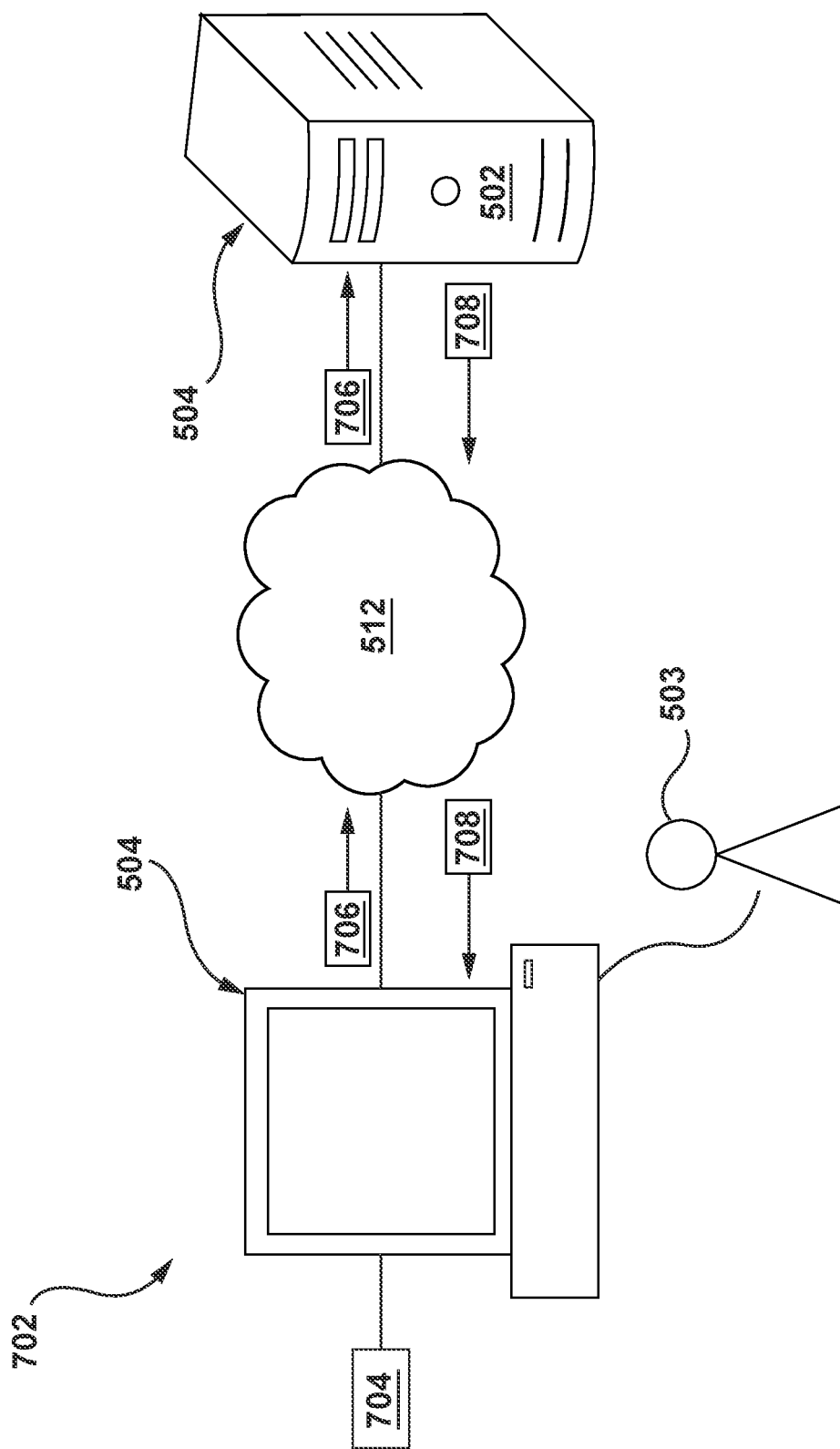
FIG. 7 depicts a schematic diagram of how communication between the server and a first set of users, providing preliminary orthodontic treatment plan, is organized within the distributed computer system of FIG. 5, in accordance with certain embodiments of the present technology.

With reference to FIG. 7, there is depicted a schematic diagram of communication between the given one of the first set of user 503 and the server 502 within the distributed computer system 500, in accordance with certain non-limiting embodiments of the present technology.

As alluded to above, in accordance with certain non-limiting embodiments of the present technology, to generate the preliminary version of the orthodontic treatment plan, the server 502 can be configured to (1) receive, from a first production electronic device 702 of the given one of the first set of users 503, the subject's data; and (2) based on the subject's data, generate, using the digital treatment planning application 504, the preliminary version of the orthodontic treatment.

It should be noted that the distributed computer system 500, including the server 502 and the manufacture electronic devices of each one of the first set of users 503, the second set of users 505, and the third set of users 507, can be configured for receiving the image data pertaining to the subject's intraoral anatomy of the subject's data from a one or more other electronic devices (not depicted). Some of such electronic devices can be used for capturing and/or processing data pertaining to maxillofacial and/or cranial anatomy of the subject. In certain embodiments, the image data received from such devices is indicative of properties of anatomical structures of the subject, including: teeth, intraoral mucosa, maxilla (such as the upper arch form 11), mandible (such as the lower arch form 10), temporomandibular joint, and nerve pathways, among other structures. In some non-limiting embodiments of the present technology, at least some of the image data is indicative of properties of external portions of the anatomical structures, for example dimensions of a gingival sulcus, and dimensions of an external portion of a tooth (e.g., a crown of the tooth) extending outwardly of the gingival sulcus. In some embodiments, the image data is indicative of properties of internal portions of the anatomical structures, for example volumetric properties of bone surrounding an internal portion of the tooth (e.g., a root of the tooth) extending inwardly of the gingival sulcus. Under certain circumstances, such volumetric properties may be indicative of periodontal anomalies which may be factored into an orthodontic treatment plan. In some non-limiting embodiments of the present technology, the image data includes cephalometric image datasets. In some embodiments, the image data includes datasets generally intended for the practice of endodontics. In some embodiments, the image data includes datasets generally intended for the practice of periodontics.

In some non-limiting embodiments of the present technology, the first manufacture electronic device 602 can be configured to receive the subject's data from an external memory device, for example, via the one or more internal and/or external buses 160 of the computing environment 100 of FIG. 4.

In some non-limiting embodiments of the present technology, the first manufacture electronic device 702 may be configured to receive the image data associated with the subject directly from an imaging device 704 communicatively coupled thereto. Broadly speaking, the first production electronic device 702 can be configured to cause the imaging device 704 to capture and/or process the image data of the lower teeth 12 and the periodontium (not depicted) of the subject. In certain non-limiting embodiments of the present technology, the image data may include, for example, one or more of: (1) images of external surfaces of respective crown portions of the lower teeth 12, (2) images of an external surface of the periodontium including those of the lower gingiva 14, the alveolar mandibular bone (not depicted), and images of superficial blood vessels and nerve pathways associated with the lower teeth 12; and (3) images of an oral region. By doing so, the imaging device 704 may be configured, for example, to capture image data of the lower arch form 10 of the subject. In another example, the imaging device may also be configured to capture and/or process image data of an upper arch form 11 associated with the subject without departing from the scope of the present technology. It should be noted that the image data may include two-dimensional (2D) data and/or three-dimensional data (3D). Further, in certain non-limiting embodiments of the present technology, the image data includes 2D data, from which 3D data may be derived, and vice versa.

In some non-limiting embodiments of the present technology, the imaging device 704 may comprise an intra-oral scanner enabling to capture direct optical impressions of the at least one of the lower arch form 10 and the upper arch form 11 of the subject.

In a specific non-limiting example, the intraoral scanner can be of one of the types available from MEDIT, CORP. of 23 Goryeodae-ro 22-gil, Seongbuk-gu, Seoul, South Korea. It should be expressly understood that the intraoral scanner can be implemented in any other suitable equipment.

In other non-limiting embodiments of the present technology, the imaging device 704 may comprise a desktop scanner enabling to digitize a mold (not depicted) representing the given configuration of the at least one of the lower arch form 10 and the upper arch form 11 associated with the respective stage of the orthodontic treatment. In this regard, the mold may have been obtained via dental impression using a material (such as a polymer, e.g. polyvinyl-siloxane) having been imprinted with the shape of the intraoral anatomy it has been applied to. In the dental impression, a flowable mixture (i.e., dental stone powder mixed with a liquid in certain proportions) may be flowed such that it may, once dried and hardened, form the replica.

In a specific non-limiting example, the desktop scanner can be of one of the types available from DENTAL WINGS, INC. of 2251, ave Letourneux, Montreal (QC), Canada, H1V 2N9. It should be expressly understood that the desktop scanner can be implemented in any other suitable equipment.

In yet other non-limiting embodiments of the present technology, the imaging device 704 can comprise a 3D laser scanner enabling to obtain a respective point cloud 3D digital model of the at least one of the lower arch form 10 and the upper arch form 11—such as by scanning the mold thereof and thus registering three-dimensional coordinates of points representative of the surface of the mold.

In a specific non-limiting example, the 3D laser scanner can be of one of the types available from LASER DESIGN of 5900 Golden Hills Drive, Minneapolis, Minn. 55416. It should be expressly understood that the desktop scanner can be implemented in any other suitable equipment.

In yet other non-limiting embodiments of the present technology, the imaging device 704 may comprise a cone beam computed tomography (CBCT) scanner. Generally speaking, the CBCT scanner comprises software and hardware allowing for capturing data using a cone-shaped X-ray beam by rotating around the subject's head. This data may be used to reconstruct 3D digital models of the following regions of the subject's anatomy: dental (teeth and gum, for example); oral and maxillofacial region (mouth, jaws, and neck); and ears, nose, and throat ("ENT").

In a specific non-limiting example, the CBCT scanner can be of one of the types available from 3SHAPE, PRIVATE LIMITED COMPANY of Holmens Kanal 7, 1060 Copenhagen, Denmark. It should be expressly understood that the CBCT scanner can be implemented in any other suitable equipment.

Further, it is contemplated that the first production electronic device 702 may be configured for processing of the received image data. The resulting image data of the lower arch form 10 and the upper arch form 11 received by the first production electronic device 702 is typically structured as a binary file or an ASCII file, may be discretized in various ways (e.g., point clouds, polygonal meshes, pixels, voxels, implicitly defined geometric shapes), and may be formatted in a vast range of file formats (for example, STL, OBJ, PLY, DICOM, and various software-specific, proprietary formats). Any image data file format is included within the scope of the present technology.

Thus, having received the subject's data, the first production electronic device 702 can be configured to generate a first data packet 706 for transmission thereof, via the communication network 512, to the server 502.

Further, after receiving the first data packet 706, the server 502 can be configured to generate, based on the subject's data, using the digital treatment planning application 504, the preliminary version of the orthodontic treatment plan. More specifically, the server 502 can be configured to preliminarily model tooth movements of at least some of the lower teeth 12 and the upper teeth 13 of the subject to target positions thereof associated with their alignment. In specific non-limiting embodiments of the present technology, to determine the preliminary version of the orthodontic treatment plan, the server 502 may be configured to apply one or more approaches described in a co-owned U.S. Pat. No. 10,993,782 issued on May 4, 2021, and entitled "SYSTEMS AND METHODS FOR DETERMINING A TOOTH TRAJECTORY,", the content of which is incorporated herein by reference in its entirety.

In other non-limiting embodiments of the present technology, to determine the preliminary version of the orthodontic treatment plan, the server 502 can be configured to execute one or more methods described in a co-owned U.S. patent application Ser. No. 17/338,143 filed on Jun. 3, 2021 and entitled "SYSTEMS AND METHODS FOR DETERMINING AN ORTHODONTIC TREATMENT", content of which is incorporated herein by reference in its entirety.

In some non-limiting embodiments of the present technology, the server 502 may be configured to generate the preliminary version of the orthodontic treatment plan in a form of a of a schedule defining movements of each of the lower teeth 12 and the upper teeth 13 of the subject.

Figure 8:
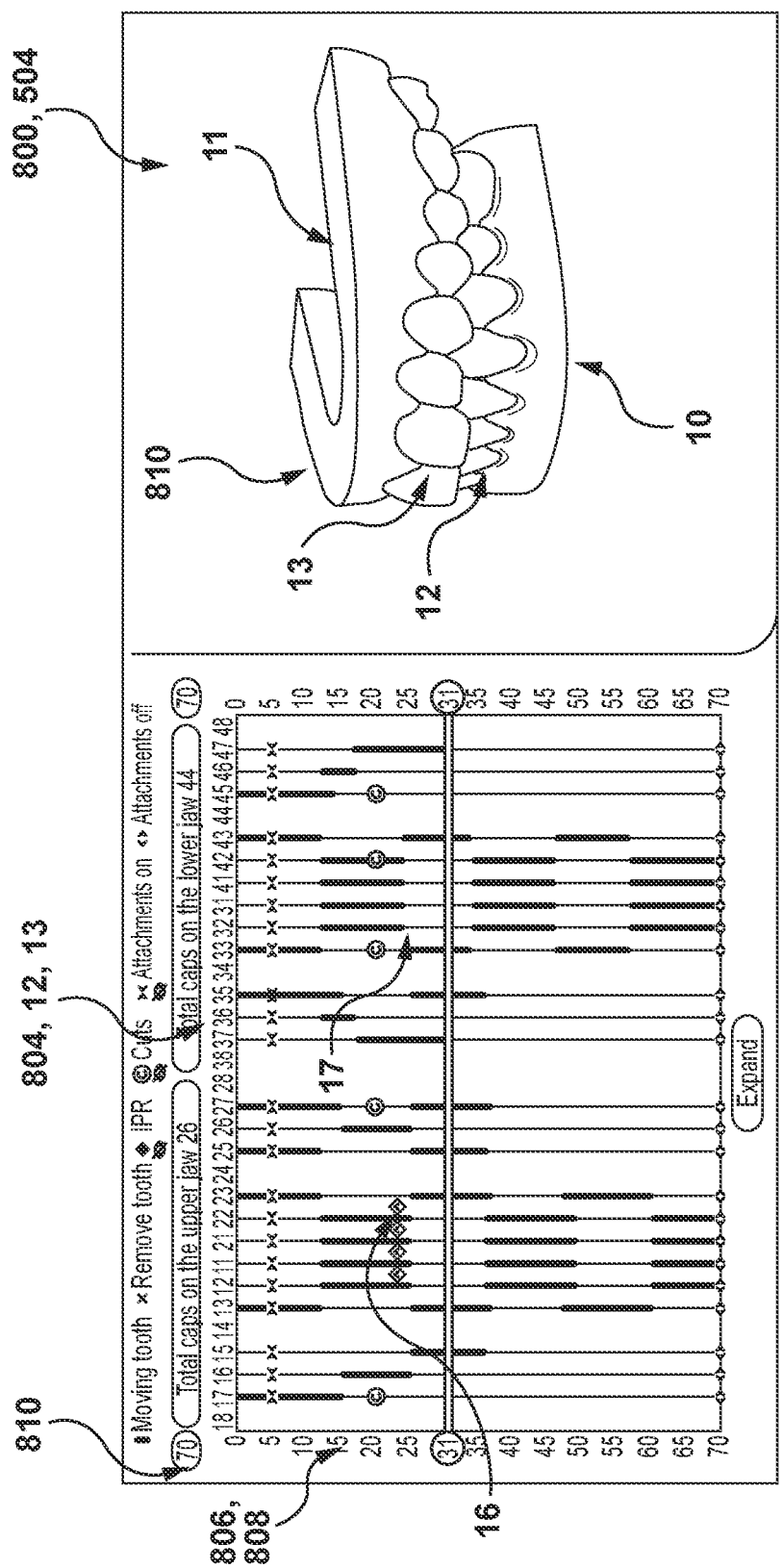
FIG. 8 depicts another example interface of the digital treatment planning application run at the server of the distributed computer system of FIG. 5 and used for planning the orthodontic treatment for treating the malocclusions depicted in FIG. 1, in accordance with certain non-limiting embodiments of the present technology.

With reference to FIG. 8, there is depicted the setup interface 800 of the digital treatment planning application 504, in accordance with certain non-limiting embodiments of the present technology.

As it can be appreciated, in some non-limiting embodiments of the present technology, the setup interface 800 may include a planned schedule 802 of the preliminary version of the orthodontic treatment plan, and the 3D digital model 810 representative of current configurations of the lower arch form 10 and the upper arch form 11 of the subject.

In the depicted embodiments of FIG. 8, the planned schedule 802 includes a horizontal axis 804 representative of respective ordinal numbers of the lower teeth 12 and the upper teeth 13; and a vertical axis 806 representative of a plurality of predetermined treatment intervals 808 of the orthodontic treatment. Accordingly, each one of the lower teeth 12 and upper teeth 13 may thus be associated with a respective trajectory defining movements thereof along an associated plurality of segments, within respective ones of the plurality of predetermined treatment intervals.

In some non-limiting embodiments of the present technology, each of the plurality of predetermined treatment intervals 808 may be associated with using a respective configuration of the aligner 20 configured to apply, during a respective one of the plurality of predetermined treatment intervals 808, respective forces onto at least one of the lower teeth 12 and the upper teeth 13 causing them to move along respective segments of their associated trajectories. In some non-limiting embodiments of the present technology, each one of the plurality of predetermined treatment intervals 808 may be equal and comprise, for example, 14 days. However, in other non-limiting embodiments of the present technology, based on specifics of a particular orthodontic treatment, the plurality of predetermined treatment intervals 808 may include predetermined treatment intervals of various durations which may be less than or more than 14 days.

Thus, once the server 502 has generated the preliminary version of the orthodontic treatment plan, the server 502 may further be configured to store it in its local memory (such as the solid-state drive 120 of the computing environment 100 of FIG. 4) for providing the collaborative access thereto to each one of the first set of users 503, the second set of users 505, and the third set of users 507, via the patient list interface 600 under their user accounts with the digital treatment planning application 504, as described above with reference to FIG. 6.

For example, in some non-limiting embodiments of the present technology, the server 502 can be configured to provide the collaborative access to the preliminary version of the orthodontic treatment plan on the respective request submitted, via the patient list interface 600 of the digital treatment planning application 504, by transmitting at least some data indicative of the preliminary version to a requesting one of the production electronic devices.

To that end, having received the respective request to access the preliminary version of the orthodontic treatment plan, the server 502 can be configured to determine a next one of the given one of the first set of users 503, the given one of the second set of users 505, and the given one of the third set of users 507, to access the preliminary version of the orthodontic treatment plan. To that end, as mentioned above, the server 502 can be configured to access the given predetermined rule of access. For example, based on the given predetermined rule of access, the server 502 can be configured to determine the next user as being the given one of the second set of users 505. Further, as mentioned above, the server 502 may further be configured to assign the first value to the status field 606 of the patient list interface 600 described above in the respective record associated with the orthodontic treatment plan, thereby granting the respective request only if it has been submitted from a respective production electronic device of the given one of the second set of users 505 (such as a second production electronic device 902 described below). As mentioned further above, in this regard, the first value of status field 606 may be indicated, for example, by the icon "Pending approval" (not depicted) in the respective record associated with the orthodontic treatment plan.

To that end, referring back to FIG. 7, the server 502 can be configured to generate a second data packet 708 including at least some data indicative of the preliminary version of the orthodontic treatment plan. The server 502 can further be configured to transmit the second data packet 708 to the requesting one of the production electronic devices for accessing the preliminary version of the orthodontic treatment plan stored at the server 502 via the setup interface 800, as mentioned above.

Reviewing and Revising the Preliminary Orthodontic Treatment Plan

Figure 9:
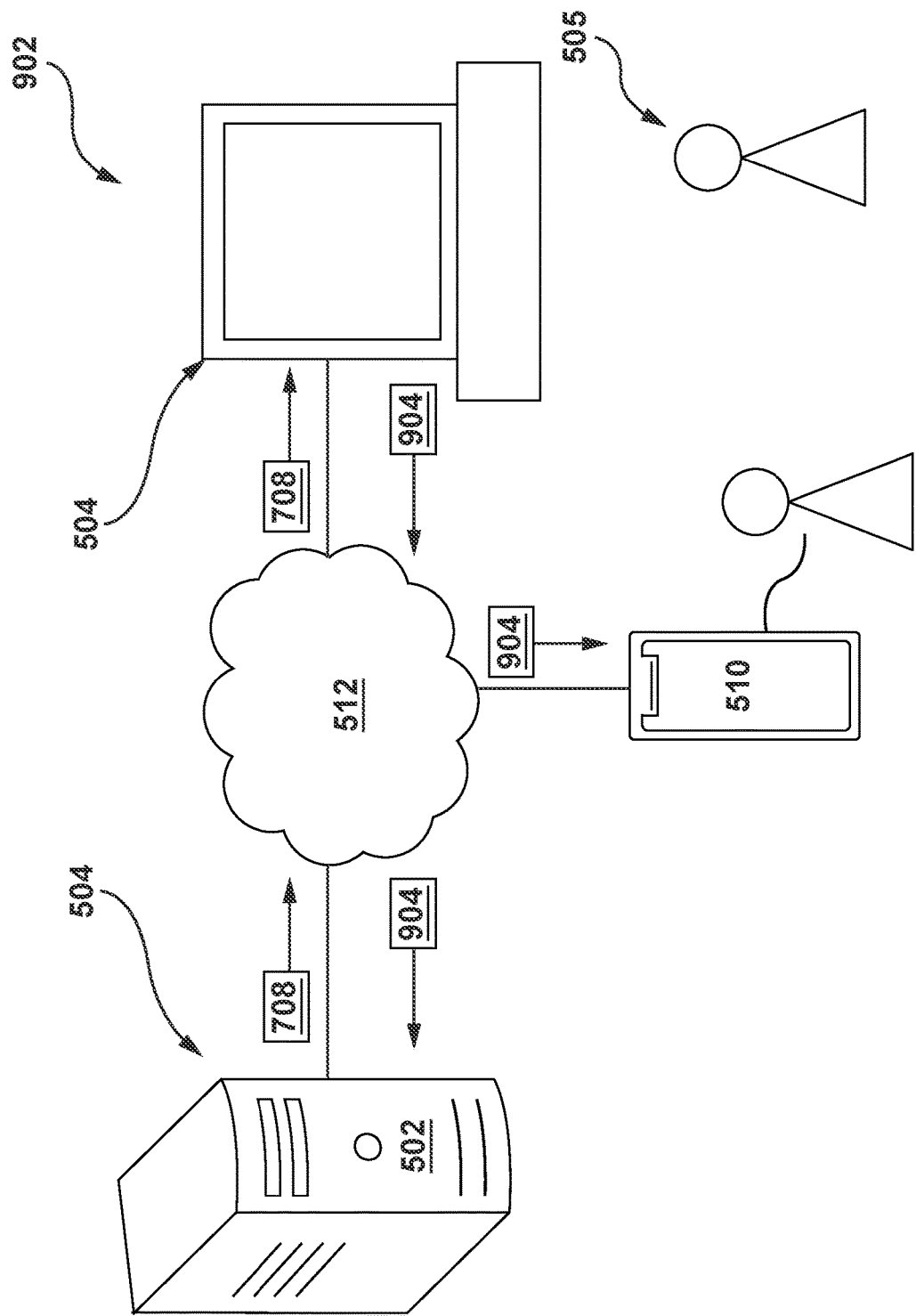
FIG. 9 depicts schematic diagram of how communication between the server and a second set of users, providing corrections to the preliminary orthodontist treatment plan, is organized within the distributed computer system of FIG. 5, in accordance with certain embodiments of the present technology.

With reference to FIG. 9, there is depicted a schematic diagram of communication between the given one of the second set of users 505 and the server 502 within the distributed computer system 500, in accordance with certain non-limiting embodiments of the present technology.

As mentioned above, in some non-limiting embodiments of the present technology, the given one of the second set of users 505 may request access, via the patient list interface 600, from the second production electronic device 1002, to the preliminary version of the orthodontic treatment plan stored on the server 502. To that end, if the preliminary version is not checked by any user, the server 502 may be configured to transmit the second data packet 708 to the second production electronic device 1002 of the given one of the second set of users 505, thereby granting access thereto to the preliminary version of the orthodontic treatment plan.

As mentioned above, in some non-limiting embodiments of the present technology, to prevent version conflict, during the time of checking the preliminary version of the orthodontic treatment by the given one of the second set of users 505, the server 502 can be configured to restrict access to the preliminary version of the orthodontic treatment, via the patient list interface 600 of the digital treatment planning application 504 described above, to any other user, such as that of the first set of users 503, the second set of users 505, and the third set of users 507, but the given one of the second set of users 505. By so doing, the server 502 can be configured to lock the preliminary version of the orthodontic treatment for possible corrections thereof from the given one of the second set of users 505.

Thus, upon receipt of the second data packet 708, the given one of the second set of users 505 can gain access to the preliminary version of the orthodontic treatment plan for review and possible revisions via the setup interface 800 of the digital treatment planning application 504. For example, in some non-limiting embodiments of the present technology, based on their experience and expertise, the given one of the second set of users 505 can introduce one or more changes to the preliminary version of the orthodontic treatment plan.

More specifically, in some non-limiting embodiments of the present technology, referring back to FIG. 8, using the planned schedule 802 in the setup interface 800, the given one of the second set of users 505 can modulate at least some of the plurality of predetermined treatment intervals 808. Also, using the planned schedule 802, in some non-limiting embodiments of the present technology, the given one of the second set of users 505 can change a sequence of moving of at least some of the lower teeth 12 and the upper teeth 13 of the subject.

In some non-limiting embodiments of the present technology, the digital treatment planning application 504 can be configured to enable the given one of the second set of users 505 to (i) plan separations (such as by interproximal reduction) between adjacent ones of the subject's teeth using the 3D digital model 810; (ii) delete and/or add attachments (such as those for increasing applied forces) on at least some of the lower teeth 12 and the upper teeth 13; and (iii) plan application of additional orthodontic appliances.

Thus, according to some non-limiting embodiments of the present technology, such modifications may be reflected onto the planned schedule 802 in changed movement trajectories of respective ones of the lower teeth 12 and the upper teeth and/or duration of replacements thereof to their target positions, for which different configurations of the aligner 20 may be required.

Further, in some non-limiting embodiments of the present technology, for introducing certain changes, the given one of the second set of users 505 may request additional image data (for example, using respective actuators in the setup interface 800, not depicted) be submitted by the given one of the first set of users 503. To that end, the server 502 can be configured to assign another value to the status field 606 for the respective record of the patient list interface 600 indicated, for example, by an icon "Further input required" (not depicted). By doing so, the server 502 can be configured to allow access to the current version of the orthodontic treatment plan only by the given one of the first set of users 503.

However, in other non-limiting embodiments of the present technology, the digital treatment planning application 504 may enable, via the setup interface 800, the given one of the second set of users 505 to reject the preliminary version of the orthodontic treatment plan altogether and request complete re-generation thereof by the given one of the first set of users 503 as described above. In these embodiments, the server 502 can be configured to assign yet another value to the status field 606 in the respective record associated with the orthodontic treatment plan of the patient list interface 600 indicated, for example, by an icon "To be re-generated based on updated data" (not depicted), thereby allowing access only by the given one of the first set of users 503, as well.

Thus, according to some non-limiting embodiments of the present technology, by reviewing and revising the preliminary version of the orthodontic treatment plan, the given one of the second set of users 505 may generate the finalized version of the orthodontic treatment plan.

To that end, referring back to FIG. 9, the second production electronic device 902 of the given one of the second set of users 505 may be configured to generate a third data packet 904 including data indicative of the finalized version of the orthodontic treatment plan for transmission thereof to the server 502. Further, having received the third data packet 904, the server 502 can further be configured to store the finalized version of the orthodontic treatment plan in its local memory.

As mentioned above, according to some non-limiting embodiments of the present technology, once the finalized version of the orthodontic treatment plan has been released by the given one of the second set of users 505, the server 502 may be configured to provide access to the finalized version of the orthodontic treatment based on the given predetermined rule of access. For example, the server 502 could be configured to determine the subject as being the next one to access orthodontic treatment plan. To that end, based on the respective request form the patient electronic device 510, the server 502 can be configured to transmit the third data packet 904 thereto, thereby granting access to the subject to the finalized version of the orthodontic treatment plan. As it can be appreciated, in some non-limiting embodiments of the present technology, to provide the subject with the most up-to-date information regarding the planned orthodontic treatment, the finalized version of the orthodontic treatment plan may also be locked for any changes by any one of the first set of users 503, the second set of users 505, and the third set of users 507 during the time it being is checked by the subject.

Figure 10:
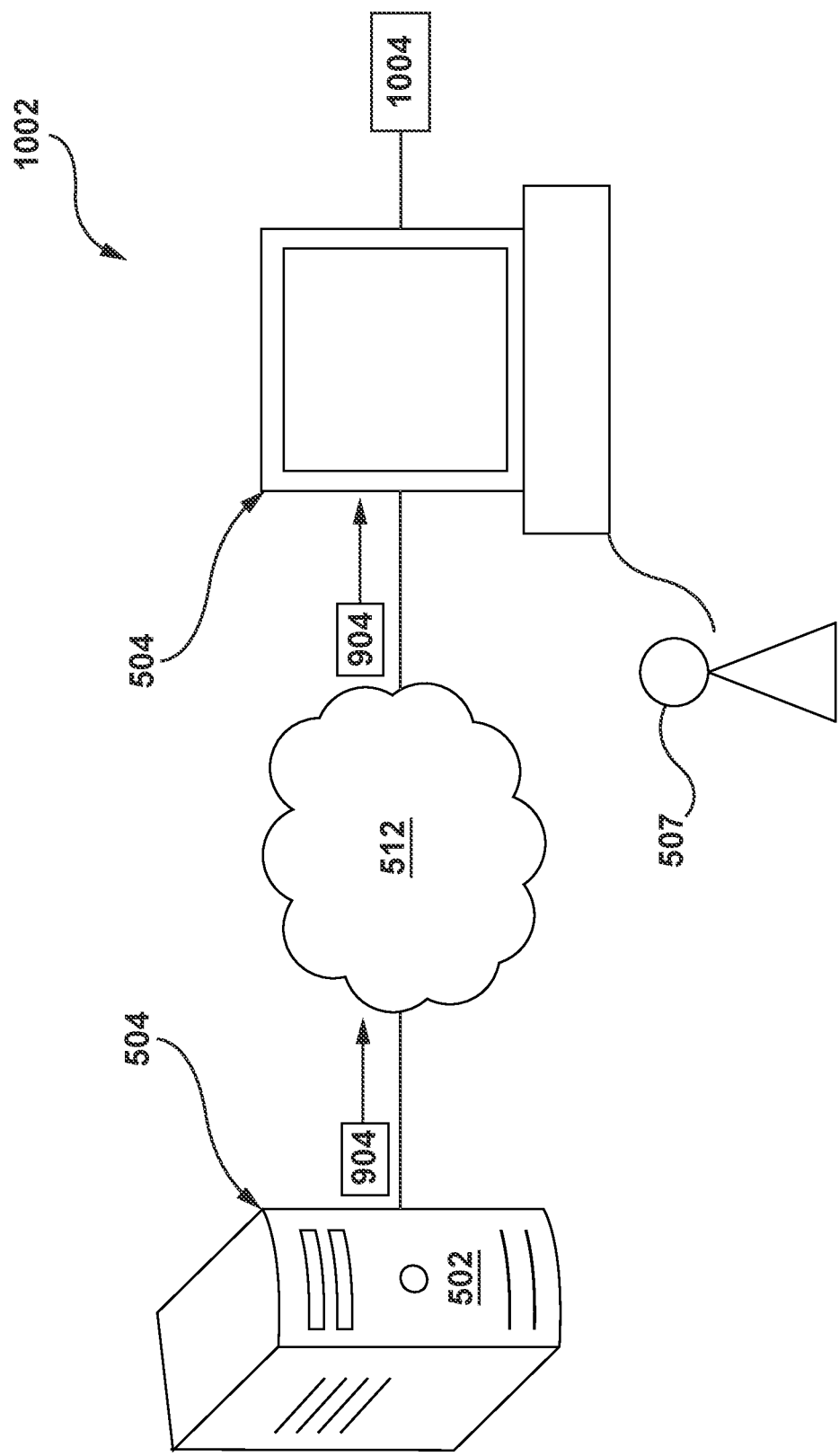
FIG. 10 depicts a schematic diagram of how communication is organized, within the distributed computer system of FIG. 5 between the server and a third set of users, for manufacturing the orthodontic appliance of FIGS. 2 and 3 in accordance with a finalized orthodontic treatment plan provided by the second set of users, in accordance with certain embodiments of the present technology.

Further, in some non-limiting embodiments of the present technology, once the subject has reviewed the finalized version of the orthodontic treatment plan and has provided necessary inputs, the server 502 could be configured, based on the predetermined rule of access, to determine the given one of the third set of users 507 as being the next user to access the orthodontic treatment plan, who can further gain access thereto upon submitting the respective request via the patient list interface 600, as described above, for manufacturing the at least one configuration of the aligner 20 in accordance with the finalized version of the orthodontic treatment, which will be described below with reference to FIG. 10.

Version Control of the Orthodontic Treatment Plan

It should be noted that, in at least some non-limiting embodiments of the present technology, the process of developing the orthodontic treatment plan may be iterative with a number of changes being input to a given version of the orthodontic treatment plan by the given one of the second set of users 505 at subsequent reviews, which may result in multiple intermediate versions of the orthodontic treatment plan before the finalized version thereof is approved.

According to certain non-limiting embodiments of the present technology, when storing each new version of the orthodontic treatment plan, the server 502 could be configured to entirely replace the previous version therewith. However, in other non-limiting embodiments of the present technology, the server 502 could be configured to save only changes made to a given previous version of the orthodontic treatment plan.

In this regard, in some non-limiting embodiments of the present technology, the server 502 could be configured to apply a hash function to a metadata structure of a respective new version of the orthodontic treatment plan to determine if any changes have been made to the given previous version of the orthodontic treatment plan. It is not limited how the hash function applied by the server 502 could be implemented; and in some non-limiting may include, for example, an MD5 hash function, an MD4 has function, a Tiger hash function, a Skein hash function, and the like.

Thus, in some non-limiting embodiments of the present technology, the server 502 could be configured to create the respective new version of the orthodontic treatment plan provided any changes have been made to the given previous version thereof. Accordingly, in these embodiments, if, for example, the given one of the second set of users 505 has not made any changes to the preliminary version of the orthodontic treatment plan, it may be used as the finalized version of the orthodontic treatment plan.

To that end, in some non-limiting embodiments of the present technology, the server 502 may be configured to apply the approach to saving changes made to each previous version as described above. By so doing, the server 502 can be configured to save computational resources thereof on saving, replacing, and transmitting, via the communication network 512, full versions of the orthodontic treatment plan.

Further, in some non-limiting embodiments of the present technology, the server 502 can be configured to save indications of past interactions of each one of the second set of users 505 with past orthodontic treatment plans for developing further orthodontic treatment plans. For example, in some non-limiting embodiments of the present technology, such interactions may include changes made to past orthodontic treatment plans by each one of the second set of users 505. For example, in some non-limiting embodiments of the present technology, the server 502 may be configured to save the changes in association with respective users that made them to generate a training set of data including a plurality of training objects for training a machine-learning algorithm (MLA). According to some non-limiting embodiments of the present technology, a given training object of the training set may include (1) an indication of a given past user (such as a respective user ID thereof in the digital treatment planning application 504); (2) an original version of a given past orthodontic treatment plan for a given past subject, before the given past user has made any change thereto; and (3) at least one subsequent version of the given past orthodontic treatment plan including at least some past changes made by the given past user.

More specifically, to generate the given training object, in some non-limiting embodiments of the present technology, the server 502 could be configured to analyze the original version of the given past orthodontic treatment plan and the at least one subsequent version thereof to register (i) changes in spatial positions (such as respective Cartesian coordinates) of respective 3D digital models of given past subject's teeth, such as within a respective 3D digital model of their arch forms (similar to the 3D digital model 810, as an example); and (2) indications of respective actions of the given past user in the digital treatment planning application 504 that caused those changes.

Accordingly, in some non-limiting embodiments of the present technology, the server 502 could be configured to train, based on the training set of data, the MLA to generate customized suggests in respect of possible changes to be made for the respective users when they access a given version of a further orthodontic treatment plan.

By way of example, and not as a limitation, in some non-limiting embodiments of the present technology, the MLA could be implemented based on neural networks (NN), convolutional neural networks (CNN), decision tree models, gradient boosted decision tree based MLA, association rule learning based MLA, Deep Learning based MLA, inductive logic programming based MLA, support vector machines based MLA, clustering based MLA, Bayesian networks, reinforcement learning based MLA, representation learning based MLA, similarity and metric learning based MLA, sparse dictionary learning based MLA, genetic algorithms based MLA, and the like. For training the MLA, the server 502 may employ a supervised-learning approach without departing from the scope of the present technology.

Further, in some non-limiting embodiments of the present technology, the server 502 can be configured to apply the so trained MLA to provide suggestions to users making changes to the given version of the further orthodontic treatment plan via the digital treatment application 504.

Referring back to the example of making changes to the preliminary version of the orthodontic treatment plan, once the given one of the second set of users 505 gains access to the preliminary version of the orthodontic treatment plan, the server 502 could be configured to apply the trained MLA to generate suggestions in respect of at least some changes to be made by the given one of the second set of users 505 to the preliminary version of the orthodontic treatment plan. More specifically, if, based on past interactions of the given one of the second set of users 505 with the past orthodontic treatment plans, the server 502 has determined that the given one of the second set of users 505 prefers using additional orthodontic appliances, such as attachments, by applying the trained MLA, the server 502 may be configured to provide, via the digital treatment planning application 504, at some point of modifying the preliminary version, a suggestion in respect of adding one or more attachments to the at least one configuration of the aligner 20. Such a suggestion may not only be a general recommendation towards using the attachments; but to the contrary, the server 502 can be configured, based on the past interactions of the given one of the second set of users 505, to determine that the given one of the second set of users 505 prefers using the attachments for specific teeth (such as molars, for example); and, using the trained MLA, the server 502 can be configured to provide the suggestions for using the one or more attachments for respective ones of the lower teeth 12 and the upper teeth 13 of the subject.

As another example, referring back to FIG. 8, based on the past interactions with the past orthodontic treatment plans, the server 502 may be configured to determine that the given one of the second set of users 505 prefers extending at least some of the plurality of predetermined treatment intervals 808 associated with a specific group of teeth (such as incisors, for example). Thus, the server 502 can further be configured, using the trained MLA, to provide suggestions to the given one of the second set of users 505 working on the preliminary version of the orthodontic treatment plan to extend the at least some of the plurality of predetermined treatment intervals 808 associated with respective ones of the lower teeth 12 and the upper teeth 13 of the subject corresponding to the specific group of teeth.

It should be expressly understood that how the provision of the suggestions described above is implemented is not limited. For example, in some non-limiting embodiments of the present, a given suggestion may be provided via a respective screen tip message (not depicted) in the setup interface 800 of the digital treatment planning application 504 while the given one of the second of users 505 is working on the preliminary version of the orthodontic treatment plan. In these embodiments, the respective screen tip message (not depicted) can be triggered by a predetermined action. For example, the suggestion to extend the at least some of the plurality of predetermined treatment intervals 808 described above may be provided once the given one of the second set of users 505 commences (or finishes) modifying the orthodontic treatment plan in respect of those respective ones of the lower teeth 12 and the upper teeth 13 corresponding to the specific group of teeth. More specifically, such a suggestion may be provided, without limitation, in response to the given one of the second set of users 505 interacting with (selecting, moving, and the like) a respective 3D digital model of at least one tooth corresponding of the specific group in the 3D digital model 810 or modifying a respective one of the plurality of predetermined treatment intervals 808 associated therewith.

In another example, the server 502 could be configured, based on the past interactions of the given one of the second set of users 505, to learn a sequence in which the given one of the second set of users 505 usually makes changes to orthodontic treatment plans. In this regard, in some non-limiting embodiments of the present technology, the server 502 can be configured to provide, using the trained MLA, the suggestions one by one, in accordance with the learnt sequence, before or after implementing each following change to the preliminary version of the orthodontic treatment plan.

In other non-limiting embodiments of the present technology, the server 502 can be configured to implement the suggestions by default once the given one of the second set of users 505 accesses the preliminary version of the orthodontic treatment plan via the setup interface 800 of the digital treatment planning application 504. In these embodiments, the server 502 can further be configured to generate a respective message (not depicted) informing the given one of the second set of users 505 of implementing the suggestions and further offering to cancel one or more thereof if need be.

Thus, in some non-limiting embodiments of the present technology, the server 502 could be configured to consider preferences in respect of corrections to orthodontic treatment plans provided by each one of the second set of users 505, thereby learning a specific style thereof, in a sense, and further use the data of such preferences to provide further suggests to each one of the second set of users 505 when developing the further orthodontic treatment plans. This may help to reduce time spent on development of the further orthodontic treatment plans, thereby increasing overall efficiency of the process for the manufacturing the aligner 20.

Manufacturing the Aligner

With reference to FIG. 10, there is depicted a schematic diagram of communication between the given one of the third set of users 507 and the server 502 within the distributed computer system 500, in accordance with certain non-limiting embodiments of the present technology.

As mentioned above, once the finalized version of the orthodontic treatment plan has been released, the given one of the third set of users 507 can request access thereto from a third production electronic device 1002, via the patient list interface 600 of the digital treatment planning application 504. To that end, the server 502 can be configured to transmit the third data packet 904 to the third production electronic device 1002, thereby providing access to the given one of the third set of user 507 to the finalized version of the orthodontic treatment plan, in accordance with which the given one of the third set of users 507 can manufacturer the at least one configuration of the aligner 20. As further mentioned above, in some non-limiting embodiments of the present technology, the server 502 can further be configured to assign yet another value to the status filed 606 in the respective record corresponding to the orthodontic treatment plan in the patient list interface 600, which may be indicated therein, for example, by an icon "Manufacture in progress" (not depicted). To that end, in some non-limiting embodiments of the present technology, by assigning this value of the status field 606, the server 502 is configured to restrict access to the finalized version of the orthodontic treatment plan by any one of the given one of the first set of users 503, the given one of the second set of users 505, and the subject via the patient list interface 600 on their respective electronic devices.

In some non-limiting embodiments of the present technology, to manufacture the at least one configuration of the aligner 20, the given one of the third set of user 507 can use the third production electronic device 1002 running appropriate software (such as CAD/CAM software) configured for generating a respective 3D digital model of the at least one configuration of the aligner 20 based on the finalized version of the orthodontic treatment plan. Further, according to some non-limiting embodiments of the present technology, the third production electronic device 1002 may be communicatively coupled, via a respective communication link, to a manufacturing device 1004 configured for fabricating the at least one configuration of the aligner 20 based on the respective 3D digital model thereof.

As described above, in some non-limiting embodiments of the present technology, the manufacturing device 1004 may be a 3D printer. In a specific non-limiting example, the 3D printer can be of one of the types available from SPRINTRAY INC. of 2705 Media Center Drive, Suite #100A, Los Angeles, Calif. 90065. It should be expressly understood that the 3D printer can be implemented in any other suitable equipment.

In other non-limiting embodiments of the present technology, the manufacturing device 1004 can be a thermoforming machine. In a specific non-limiting example, the 3D printer can be of one of the types available from HAMER INC. of Rambla Antoni Gaudi, 108792 La Granada (Barcelona) Spain. It should be expressly understood that the thermoforming machine can be implemented in any other suitable equipment.

It should be noted that in some non-limiting embodiments of the present technology, additional devices and systems may be communicatively coupled to the third production electronic device 1002 for executing additional operations relating to the manufacturing the at least one configuration of the aligner 20. For example, the additional devices and systems may include those for trimming the at least one configuration of the aligner 20 after manufacturing a preform thereof.

In specific non-limiting embodiments of the present technology, the trimming the at least one configuration of the aligner 20 may be implemented as described in a co-owned U.S. patent application Ser. No. 16/704,718 filed on Dec. 5, 2019, entitled "SYSTEMS AND METHODS FOR FORMING PERSONALIZED DENTAL APPLIANCES", the content of which is hereby incorporated by reference in its entirety Thus, once the at least one configuration of the aligner 20 has been manufactured, it may further be shipped to the subject for implementation of the orthodontic treatment in accordance with the finalized version of the orthodontic treatment plan. Further, as it can be appreciated, in some non-limiting embodiments of the present technology, the server 502 can be configured to assign yet another value to the status field 606 in the respective record corresponding to the orthodontic treatment plan in the patient list interface 600 described above, thereby allowing the collaborative access to the current version of the orthodontic treatment in accordance with the sequence of access defined by the given predetermined rule described above. By so doing, the server 502 could be configured to allow further possible changes to the so developed orthodontic treatment plan. For example, this value may be indicated by an icon "Completed and implemented" (not depicted).

Thus, according to certain non-limiting embodiments of the present technology, using the digital treatment planning application 504, the server 502 can be configured to organize the process of manufacturing the aligner 20 where only one of the first set of users 503, the second set of users 505, and the third set of users 507 can access the current version of the orthodontic treatment plan, stored at the server 502, at a time.

It should be expressly understood that such distribution of responsibilities, for the manufacturing the aligner 20, between the first set of users 503, the second set of users 505, and the third set of users 507, as amongst single representatives therefrom, as described above is provided only for purposes of clarity of explanation and better understanding of the present technology; and, in some non-limiting embodiments of the present technology, any number of users from any of the first set of users 503, the second set of users 505, and the third set of users 507 can be involved in the process of manufacturing the aligner 20 described above.

Further, users of any one of the first set of users 503, the second set of users 505, and the third set of users 507 and/or users within a given one of the first set of users 503, the second set of users 505, and the third set of users 507 involved in the process for the manufacturing the aligner 20 may not be affiliated with a single entity and may thus represent different entities (such as different clinics, dental/orthodontic offices, laboratories, and the like). Also, some users may combine functions of at least some of the first set of users 503, the second set of users 505, and the third set of users 507, as described above. For example, a given practitioner may combine functions of the given one of the first set of users 503 and that of the second set of users 505.

It should yet further be noted that, in specific non-limiting embodiments of the present technology, the whole process for the manufacturing the aligner 20 can be implemented by a single user combining functions of one or more of the given one of the first set of users 503, the given one of the second set of users 505, and the given one of the third set of users 507, as described above.

It should further be expressly understood that the approaches described above to the version control management of orthodontic treatment plans and the access distribution thereto may also be applied, mutatis mutandis, to cases where a given orthodontic treatment plan needs to be revised during the implementation thereof. For example, further stages of the orthodontic treatment plan may be required to be modified based on how the subject's teeth have actually been moving during past stages of the orthodontic treatment. In another example, at some stage, the orthodontic treatment may cause the subject discomfort, which also may require corrections. To that end, new image data pertaining to the subject's teeth may be obtained, and at least some of the methods described hereinabove with reference to FIGS. 6 to 9 may be reiterated given the new image data.

Method

Figure 11:
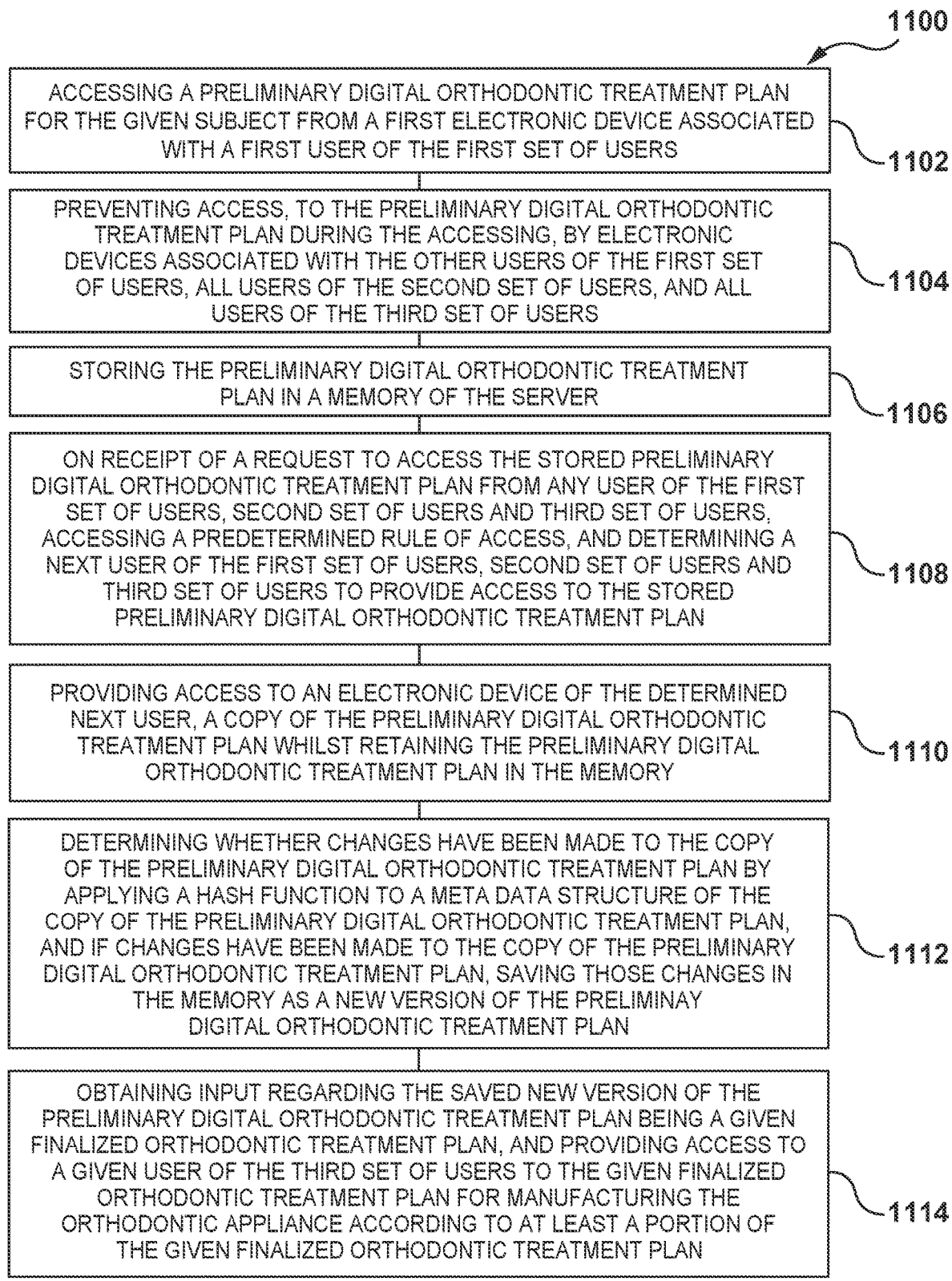
FIG. 11 depicts a flowchart of a method for manufacturing the orthodontic appliance of FIGS. 2 and 3 for treating the malocclusions depicted in FIG. 1, according to certain embodiments of the present technology.

Given the architecture and the examples provided hereinabove, it is possible to execute a method for manufacturing the aligner 20 using the distributed computer system 500. With reference now to FIG. 11, there is depicted a flowchart of a method 1100, according to certain non-limiting embodiments of the present technology. The method 1100 may be executed by the server 502 of the distributed computer system 500.

Step 1102: Accessing a Preliminary Digital Orthodontic Treatment Plan for the Given Subject from a First Electronic Device Associated with a First User of the First Set of Users The method 1100 commences at step 1102 with the given one of the first set of users 503 creating the preliminary version of the orthodontic treatment plan. As mentioned above with reference to FIG. 7, the given one of the first set of users 503 can create the preliminary version of the orthodontic treatment plan using the first production electronic device 702 having access to the digital treatment planning application 504 run on the server 502. As also mentioned above, the digital treatment planning application 504 may be a thin client application stored and run on the server 502 and accessible by user thereof via, for example, browser applications of their electronic devices.

Thus, as described further above with reference to FIG. 7, in some non-limiting embodiments of the present technology, the given one of the first set of users 503 may access the subject's data of the subject, submit the subject's data to the digital treatment planning application 504, by transmitting the first data packet 706 to the server 502, to generate the preliminary version of the orthodontic treatment plan.

Once the preliminary version of the orthodontic treatment plan has been created, the server 502 can be configured to transmit at least some data indicative thereof in the second data packet 708 to the first production electronic device 702 for presentation (and possible corrections) of the preliminary version of the orthodontic treatment plan to the given one of the first set of users 503. As mentioned above with reference to FIG. 8, the preliminary version may be presented to the given one of the first set of users 503 in the setup interface 800 of the digital treatment application 504.

The method 1100 thus proceeds to step 1104.

Step 1104: Preventing Access, to the Preliminary Digital Orthodontic Treatment Plan During the Accessing, by Electronic Devices Associated with Other Users of the First Set of Users, all Users of the Second Set of Users, and all Users of the Third Set of Users At step 1104, in some non-limiting embodiments of the present technology, while the preliminary version of the orthodontic treatment plan is checked by the given one of the first set of users 503, the server 502 could be configured to restrict access to the orthodontic treatment plan by any other user of the first set of users 503, the second set of users 505, the third set of users 507, and the subject.

As mentioned above with reference to FIG. 6, the server 502 could be configured to control access to the current version of the orthodontic treatment plan by any one of the first set of users 503, the second set of users 505, the third set of users 507, and the subject by assigning respective values of the status field 606 in the respective record associated with the orthodontic treatment plan in the patient list interface 600 of the digital treatment planning application 504.

By so doing, while the preliminary version of the orthodontic treatment plan is checked by the first one of the first set of users 503, the server 502 can be configured to make the respective record associated with the orthodontic treatment plan in the patient list interface 600 inactive (non-selectable) when it is launched form a respective user account of any other one of the first set of users 503, the second set of users 505, the third set of users 507, and the subject.

The method 1100 thus advances to step 1106.

Step 1106: Storing the Preliminary Digital Orthodontic Treatment Plan in a Memory of the Server At step 1106, once the preliminary version of the orthodontic treatment plan has been created and released by the given one of the first set of users 503, according to certain non-limiting embodiments of the present technology, the server 502 can be configured to store the preliminary version of the orthodontic treatment plan in its local memory (such as the solid-state drive 120 of the computing environment 100 of FIG. 4).

The method 1100 hence advances to step 1108.

Step 1108: On Receipt of a Request to Access the Stored Preliminary Digital Orthodontic Treatment Plan from any User of the First Set of Users, Second Set of Users and Third Set of Users, Accessing a Predetermined Rule of Access, and Determining a Next User of the First Set of Users, Second Set of Users and Third Set of Users to Provide Access to the Stored Preliminary Digital Orthodontic Treatment Plan At step 1108, the server 502 could be configured to receive a request to access the preliminary version of the orthodontic treatment plan from a given one of the first set of users 503, the second set of users 505, and the third set of users 507. As mentioned above, the request may be submitted by the given one of the first set of users 503, the second set of users 505, and the third set of users 507, under their respective user account, by selecting the respective record associated with the orthodontic treatment plan in the patient list interface 600 of the digital treatment planning application 504.

To that end, the server 502 can be configured to access the given predetermined rule of access, as described above, to determine the next one to access the preliminary version of the orthodontic treatment plan. For example, in accordance with the given predetermined rule of access, the server 502 can be configured to determine the next one to access the preliminary version as being the given one of the second set of users 505.

As mentioned hereinabove with reference to FIG. 5, the given one of the second set of users 505 may be a higher-level medical practitioner, such as, without limitations, a medical doctor, a dentist, an orthodontist, a maxillo-facial surgeon, and the like. Thus, the given one of the second set of users 505, based on their experience and expertise, can review and revise the preliminary version of the orthodontic treatment plan to generate the finalized version of the orthodontic treatment plan defining the at least one configuration of the aligner 20.

Thus, the method 1100 advances to step 1110.

Step 1110: Providing Access to an Electronic Device of the Determined Next User, a Copy of the Preliminary Digital Orthodontic Treatment Plan Whilst Retaining the Preliminary Digital Orthodontic Treatment Plan in the Memory At step 1110, once the server 502 has determined, in accordance with the given predetermined rule of access, the next one to access the preliminary version of the orthodontic treatment plan as being the given one of the second set of users 505, the server 502 may be configured to assign the first value to the status field 606 in the patient list interface 600 to make the respective record associated with the orthodontic treatment active for selection only under the user account of the given one of the second set of users 505.

Thus, the given one of the second set of users 505 may further access the preliminary version of the orthodontic treatment plan, from the second production electronic device 902 thereof, in the setup interface 800 to make one or more changes to the preliminary version of the orthodontic treatment plan, as described above with reference to FIG. 9. For example, via the setup interface 800 of the digital treatment planning application 504, the given one of the second set of users 505 may (i) plan separations (such as by interproximal reduction) between adjacent ones of the subject's teeth using the 3D digital model 810; (ii) delete and/or add attachments (such as those for increasing applied forces) on at least some of the lower teeth 12 and the upper teeth 13; and (iii) plan application of additional orthodontic appliances.

In some non-limiting embodiments of the present technology, while the given one of the second set of users 505 is working on the preliminary version of the orthodontic treatment plan, the server 502 can be configured to provide to them suggestions in respect of at least some of the changes to be made to the preliminary version of the orthodontic treatment plan.

As mentioned above, in accordance with some non-limiting embodiments of the present technology, to provide the suggestions, the server 502 can be configured to apply the MLA that has been trained, based on past user interactions with past orthodontic treatment plans as described above, to predict changes to be made by a specific user, such as the given one of the second set of users 502. By so doing, the server 502 can be configured to provide suggestions to the given one of the second set of users 505 considering their preferences towards developing orthodontic treatment plans.

Thus, by introducing the one or more changes to the preliminary version of the orthodontic treatment plan, the given one of the second set of users 505 may create the finalized version of the orthodontic treatment plan, according to which the at least one configuration of the aligner 20 may further be manufactured. To that end, as mentioned above, the second production electronic device 902 may be configured to generate the third data packet 904 including data indicative of the finalized version for transmission thereof to the server 502.

The method 1100 thus advances to step 1112.

Step 1112: Determining Whether Changes have been Made to the Copy of the Preliminary Digital Orthodontic Treatment Plan by Applying a Hash Function to a Meta Data Structure of the Copy of the Preliminary Digital Orthodontic Treatment Plan, and if Changes have been Made to the Copy of the Preliminary Digital Orthodontic Treatment Plan, Saving Those Changes in the Memory as a New Version of the Preliminary Digital Orthodontic Treatment Plan Further, at step 1112, according to certain non-limiting embodiments of the present technology, having received the third data packet 904, the server 502 may be configured not to replace the preliminary version of the orthodontic treatment plan entirely with the finalized version, but rather save only changes made to the preliminary version of the orthodontic treatment plan as the finalized version thereof. To that end, as described above, the server 502 can be configured to apply the hash function to a metadata structure of the finalized version of the orthodontic treatment plan to determine if changes to the preliminary version have been made. It is not limited how the hash function applied by the server 502 could be implemented; and in some non-limiting may include, without limitation, an MD5 hash function, an MD4 has function, a Tiger hash function, a Skein hash function, and the like.

Accordingly, in these embodiments, if, for example, the given one of the second set of users 505 has not made any changes to the preliminary version of the orthodontic treatment plan, it may be used as the finalized version of the orthodontic treatment plan.

In those embodiments where a number of intermediate versions precedes to the finalized version of the orthodontic treatment plan, such as when other ones of the second set of users provide their respective changes to the preliminary version, in some non-limiting embodiments of the present technology, the server 502 may be configured to apply the approach to saving changes made to each previous version as described above. By so doing, the server 502 can be configured to save computational resources thereof on saving, replacing, and transmitting, via the communication network 512, full versions of the orthodontic treatment plan.

The method 1100 thus proceeds to step 1114.

Step 1114: Obtaining Input Regarding the Saved New Version of the Preliminary Digital Orthodontic Treatment Plan being a Given Finalized Orthodontic Treatment Plan, and Providing Access to a Given User of the Third Set of Users to the Given Finalized Orthodontic Treatment Plan for Manufacturing the Orthodontic Appliance According to at Least a Portion of the Given Finalized Orthodontic Treatment Plan Further, once the finalized version of the orthodontic treatment plan has been saved, the server 502 can be configured to determine, in accordance with the given predetermined rule of access, the next user to access the orthodontic treatment plan as being the given one of the third set of users 507. Accordingly, by assigning the respective value to the status filed 606 in the patient list interface 600, the server 502 can be configured to make the respective record therein associated with the orthodontic treatment plan available for selection only under the user account of the given one of the third set of users 507.

Thus, as described above with reference to FIG. 10, the given one of the third set of users may access the finalized version of the orthodontic treatment plan from the third production electronic device 1002 thereof for manufacturing the at least one configuration of the aligner 20.

The method 1100 thus terminates.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

The invention claimed is:

1. A distributed computer system for manufacturing an orthodontic appliance for a subject, the system comprising:
    a server communicatively couplable to electronic devices associated with sets of users, a given electronic device being configured to implement a thin client for accessing the server, the sets of users comprising:
        a first set of users for providing preliminary orthodontic treatment plans for subjects,
        a second set of users for providing input to the preliminary orthodontic treatment plans, and
        a third set of users for manufacturing orthodontic appliances to implement at least a portion of finalized orthodontic treatment plans, the finalized orthodontic treatment plans being based on a given preliminary orthodontic treatment plan and a given input from a user of the second set of users to the given preliminary orthodontic treatment plan;
    the server having a processor configured to execute a method, the method comprising, for a given subject:
        accessing a preliminary digital orthodontic treatment plan for the given subject from a first electronic device associated with a first user of the first set of users;
        preventing access, to the preliminary digital orthodontic treatment plan during the accessing, by electronic devices associated with other users of the first set of users, all users of the second set of users, and all users of the third set of users;
        storing the preliminary digital orthodontic treatment plan in a memory of the server;
        on receipt of a request to access the stored preliminary digital orthodontic treatment plan from any user of the first set of users, second set of users and third set of users, accessing a predetermined rule of access, and determining a next user of the first set of users, second set of users and third set of users to provide access to the stored preliminary digital orthodontic treatment plan;

providing access to an electronic device of the determined next user, a copy of the preliminary digital orthodontic treatment plan whilst retaining the preliminary digital orthodontic treatment plan in the memory;

determining whether changes have been made to the copy of the preliminary digital orthodontic treatment plan by applying a hash function to a meta data structure of the copy of the preliminary digital orthodontic treatment plan, and if changes have been made to the copy of the preliminary digital orthodontic treatment plan, saving those changes in the memory as a new version of the preliminary digital orthodontic treatment plan;

obtaining input regarding the saved new version of the preliminary digital orthodontic treatment plan being a given finalized orthodontic treatment plan, and providing access to a given user of the third set of users to the given finalized orthodontic treatment plan for manufacturing the orthodontic appliance according to at least a portion of the given finalized orthodontic treatment plan.

2. The distributed computer system of claim 1, wherein the hash function comprises a sum of md5 hashes.

3. The distributed computer system of claim 1, further comprising preventing access, to the copy of the preliminary digital orthodontic treatment plan whilst the next user has access to the copy of the preliminary digital orthodontic treatment plan, by electronic devices associated with other users of the first set of users, the second set of users, and the third set of users.

4. The distributed computer system of claim 1, wherein after the new version of the preliminary digital orthodontic treatment plan is saved, on receipt of a request to access the preliminary digital orthodontic treatment plan from another given user of the first set of users, the second set of users and the third set of users, accessing the predetermined rule of access, and determining a next other user to provide access to the saved new version of the preliminary digital orthodontic treatment plan.

5. The distributed computer system of claim 1, further comprising, for a given user of the second set of users, applying a trained machine learning algorithm to provide suggested inputs to the preliminary orthodontic treatment plan according to preferences of the given user.

6. The distributed computer system of claim 1, further comprising training a machine learning algorithm on orthodontic treatment plan preferences of a given user of the second set of users for providing suggested inputs to preliminary orthodontic treatment plans according to those preferences.

7. The distributed computer system of claim 1, wherein the second set of users are orthodontic dentists or doctors.

8. The distributed computer system of claim 1, wherein certain users may be associated with more than one of the first set of users, second set of users and third set of users.

9. A server for manufacturing an orthodontic appliance for a subject, the server being communicatively couplable to electronic devices associated with sets of users, a given electronic device being configured to implement a thin client for accessing the server, the sets of users comprising:

a first set of users for providing preliminary orthodontic treatment plans for subjects, a second set of users for providing input to the preliminary orthodontic treatment plans, and a third set of users for manufacturing orthodontic appliances to implement at least a portion of finalized orthodontic treatment plans, the finalized orthodontic treatment plans being based on a given preliminary orthodontic treatment plan and a given input from a user of the second set of users to the given preliminary orthodontic treatment plan;

the server including:
a processor and
a non-transitory memory storing instructions,
the processor, upon executing the instructions, being configured to:

provide access to a preliminary digital orthodontic treatment plan for a given subject by a first electronic device associated with a first user of the first set of users;

while providing access to the preliminary digital orthodontic treatment plan by the first electronic device, prevent access to the preliminary digital orthodontic treatment plan by electronic devices associated with other users of the first set of users, all users of the second set of users, and all users of the third set of users;

store the preliminary digital orthodontic treatment plan in the non-transitory memory;

on receipt of a request to access the stored preliminary digital orthodontic treatment plan from any user of the first set of users, second set of users and third set of users, access a predetermined rule of access to determine a next user of the first set of users, second set of users and third set of users to provide access to the stored preliminary digital orthodontic treatment plan;

provide access to a copy of the preliminary digital orthodontic treatment plan by an electronic device of the determined next user, whilst retaining the preliminary digital orthodontic treatment plan in the non-transitory memory;

determine whether changes have been made to the copy of the preliminary digital orthodontic treatment plan by applying a hash function to a meta data structure of the copy of the preliminary digital orthodontic treatment plan, and if changes have been made to the copy of the preliminary digital orthodontic treatment plan, save the changes in the non-transitory memory as a new version of the preliminary digital orthodontic treatment plan;

obtain input regarding the saved new version of the preliminary digital orthodontic treatment plan being a given finalized orthodontic treatment plan and provide access to a given user of the third set of users to the given finalized orthodontic treatment plan for manufacturing the orthodontic appliance according to at least a portion of the given finalized orthodontic treatment plan.

10. The server of claim 9, wherein the processor is further configured to prevent access, to the copy of the preliminary digital orthodontic treatment plan whilst the determined next user has access to the copy of the preliminary digital orthodontic treatment plan, by electronic devices associated with other users of the first set of users, the second set of users, and the third set of users.

11. The server of claim 9, wherein after the new version of the preliminary digital orthodontic treatment plan is saved, on receipt of a request to access the preliminary digital orthodontic treatment plan from another given user of the first set of users, the second set of users and the third set of users, the processor is further configured to access the predetermined rule of access to determine a next other user to provide access to the saved new version of the preliminary digital orthodontic treatment plan.

12. The server of claim 9, wherein, for a given user of the second set of users, the processor is further configured to apply a trained machine learning algorithm to provide suggested inputs to the preliminary orthodontic treatment plan according to preferences of the given user.

13. The server of claim 9, wherein the processor is further configured to train a machine learning algorithm on orthodontic treatment plan preferences of a given user of the second set of users for providing suggested inputs to preliminary orthodontic treatment plans according to those preferences.

14. A method of manufacturing an orthodontic appliance for a subject, the method executable by a server including a processor, the server communicatively couplable to electronic devices associated with sets of users, a given electronic device being configured to implement a thin client for accessing the server, the sets of users comprising:
    a first set of users for providing preliminary orthodontic treatment plans for subjects,
    a second set of users for providing input to the preliminary orthodontic treatment plans, and
    a third set of users for manufacturing orthodontic appliances to implement at least a portion of finalized orthodontic treatment plans, the finalized orthodontic treatment plans being based on a given preliminary orthodontic treatment plan and a given input from a user of the second set of users to the given preliminary orthodontic treatment plan;
    the method comprising, for a given subject:
        providing, by the processor, access to a preliminary digital orthodontic treatment plan for the given subject by a first electronic device associated with a first user of the first set of users;
        during the providing access by the first electronic device, preventing access, to the preliminary digital orthodontic treatment plan, by electronic devices associated with other users of the first set of users, all users of the second set of users, and all users of the third set of users;
        storing, by the processor, the preliminary digital orthodontic treatment plan in a memory of the server;
        on receipt of a request to access the stored preliminary digital orthodontic treatment plan from any user of the first set of users, second set of users and third set of users, accessing, by the processor, a predetermined rule of access to determine a next user of the first set of users, second set of users and third set of users to provide access to the stored preliminary digital orthodontic treatment plan;
        providing, by the processor, access to an electronic device of the determined next user, a copy of the preliminary digital orthodontic treatment plan whilst retaining the preliminary digital orthodontic treatment plan in the memory;
        determining, by the processor, whether changes have been made to the copy of the preliminary digital orthodontic treatment plan by applying a hash function to a meta data structure of the copy of the preliminary digital orthodontic treatment plan, and if changes have been made to the copy of the preliminary digital orthodontic treatment plan, saving those changes in the memory as a new version of the preliminary digital orthodontic treatment plan;
        obtaining, by the processor, input regarding the saved new version of the preliminary digital orthodontic treatment plan being a given finalized orthodontic treatment plan, and
        providing, by the processor, access to a given user of the third set of users to the given finalized orthodontic treatment plan for manufacturing the orthodontic appliance according to at least a portion of the given finalized orthodontic treatment plan.

15. The method of claim 14, wherein the hash function comprises a sum of md5 hashes.

16. The method of claim 14, further comprising preventing, by the processor, access, to the copy of the preliminary digital orthodontic treatment plan whilst the next user has access to the copy of the preliminary digital orthodontic treatment plan, by electronic devices associated with other users of the first set of users, the second set of users, and the third set of users.

17. The method of claim 14, wherein after the new version of the preliminary digital orthodontic treatment plan is saved, on receipt of a request to access the preliminary digital orthodontic treatment plan from another given user of the first set of users, the second set of users and the third set of users, accessing, by the processor, the predetermined rule of access to determine a next other user to provide access to the saved new version of the preliminary digital orthodontic treatment plan.

18. The method of claim 14, further comprising, for a given user of the second set of users, applying a trained machine learning algorithm to provide suggested inputs to the preliminary orthodontic treatment plan according to preferences of the given user.

19. The method of claim 14, wherein a given one of the second set of users is one of an orthodontist, a dentist, and a doctor.

20. The method of claim 14, wherein certain users may be associated with more than one of the first set of users, second set of users and third set of users.

* * * * *